United States Patent
Fitzgibbon et al.

(10) Patent No.: US 11,200,298 B2
(45) Date of Patent: Dec. 14, 2021

(54) REDUCING PROBABILITY OF GLASS BREAKAGE IN DRUG DELIVERY DEVICES

(71) Applicant: AMGEN INC., Thousand Oaks, CA (US)

(72) Inventors: Sean Fitzgibbon, Camarillo, CA (US); Christopher R. Folk, San Diego, CA (US); Julian Jazayeri, Woodland Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 342 days.

(21) Appl. No.: 16/070,224

(22) PCT Filed: Mar. 14, 2017

(86) PCT No.: PCT/US2017/022249
§ 371 (c)(1),
(2) Date: Jul. 13, 2018

(87) PCT Pub. No.: WO2017/160799
PCT Pub. Date: Sep. 21, 2017

(65) Prior Publication Data
US 2019/0050375 A1    Feb. 14, 2019

Related U.S. Application Data

(60) Provisional application No. 62/308,578, filed on Mar. 15, 2016.

(51) Int. Cl.
*G06F 17/18* (2006.01)
*A61M 5/20* (2006.01)
(Continued)

(52) U.S. Cl.
CPC .......... *G06F 17/18* (2013.01); *A61M 5/2033* (2013.01); *A61M 5/315* (2013.01); *G06F 30/17* (2020.01);
(Continued)

(58) Field of Classification Search
CPC .......... G06F 17/18; G06F 30/20; G06F 30/17; G16H 20/17; A61M 5/2033; A61M 5/315
(Continued)

(56) References Cited

U.S. PATENT DOCUMENTS 5,584,827 A * 12/1996 Korteweg ........ A61B 17/12022
604/11
8,465,468 B1 * 6/2013 Pettis .................... A61M 5/158
604/506

(Continued)

FOREIGN PATENT DOCUMENTS

| EP | 2423659 A1 | 2/2012 |
| EP | 2523150 A1 | 11/2012 |
| WO | WO-03011378 A1 | 2/2003 |

OTHER PUBLICATIONS

Bressolle et al. ("A Weibull Distribution Model for Intradermal Administration of Ceftazidime", American pharmaceutical Association, 1993, pp. 1175-1178). (Year: 1993).*
(Continued)

*Primary Examiner* — Iftekhar A Khan
(74) *Attorney, Agent, or Firm* — Marshall, Gerstein & Borun LLP

(57) ABSTRACT

A method for determining predicted failure rates of drug injection devices includes receiving a set of parameters that specify physical properties of (i) a syringe, and (ii) a liquid drug, and (iii) a drug injection device configured to deliver the liquid drug to a patient via the syringe. The method further includes receiving failure rate data that specifies a
(Continued)

measured rate of failure of the drug injection device in response to various peak pressures within the syringe, applying the received set of parameters to a kinematic model of the drug injection device to determine a predicted peak pressure within the syringe, including determining the predicted peak pressure as a function of impact velocity of the liquid drug, determining a probability of failure of the drug injection device using (i) the received failure rate data and (ii) the predicted peak pressure, and providing an indication of the determined probability of failure to an output device.

16 Claims, 14 Drawing Sheets

(51) Int. Cl.
```
      G06F 30/17      (2020.01)
      G06F 30/20      (2020.01)
      G16H 20/17      (2018.01)
      A61M 5/315      (2006.01)
      A61M 5/32       (2006.01)
      G06F 111/08     (2020.01)
      G06F 111/10     (2020.01)
      G06F 17/13      (2006.01)
```
(52) U.S. Cl.
 CPC ............ *G06F 30/20* (2020.01); *G16H 20/17* (2018.01); *A61M 5/3202* (2013.01); *A61M 2005/206* (2013.01); *A61M 2205/3327* (2013.01); *A61M 2205/3331* (2013.01); *A61M 2205/3375* (2013.01); *A61M 2205/50* (2013.01); *A61M 2205/70* (2013.01); *A61M 2207/00* (2013.01); *G06F 17/13* (2013.01); *G06F 2111/08* (2020.01); *G06F 2111/10* (2020.01)

(58) Field of Classification Search
 USPC .......................................................... 703/2
 See application file for complete search history.

(56) References Cited

U.S. PATENT DOCUMENTS

| | | | | |
|---|---|---|---|---|
| 8,734,384 | B2* | 5/2014 | Boyd | A61M 5/30 |
| | | | | 604/70 |
| 9,061,097 | B2* | 6/2015 | Holt | A61M 5/14248 |
| 9,149,579 | B2* | 10/2015 | Edwards | A61M 5/2053 |
| 9,242,052 | B2* | 1/2016 | Pettis | A61K 38/28 |
| 9,987,428 | B2* | 6/2018 | Tan-Malecki | A61M 5/148 |
| 10,092,706 | B2* | 10/2018 | Denzer | A61P 7/00 |
| 10,398,854 | B2* | 9/2019 | Fenster | A61M 5/20 |
| 10,646,664 | B2* | 5/2020 | Lee | A61M 5/3287 |
| 2004/0215151 | A1* | 10/2004 | Marshall | A61M 5/322 |
| | | | | 604/198 |
| 2006/0270985 | A1* | 11/2006 | Hommann | A61M 5/31553 |
| | | | | 604/136 |
| 2008/0081994 | A1* | 4/2008 | Kim | A61B 8/06 |
| | | | | 600/438 |
| 2008/0103453 | A1* | 5/2008 | Liversidge | A61M 5/326 |
| | | | | 604/187 |
| 2010/0010454 | A1* | 1/2010 | Marshall | A61M 5/2033 |
| | | | | 604/208 |
| 2010/0082305 | A1* | 4/2010 | Fitch | G06F 30/23 |
| | | | | 703/2 |
| 2012/0219589 | A1* | 8/2012 | Garcia De Castro Andrews | A61M 37/0069 |
| | | | | 424/227.1 |
| 2012/0290104 | A1* | 11/2012 | Holt | G06Q 10/00 |
| | | | | 700/29 |
| 2012/0323177 | A1* | 12/2012 | Adams | A61M 5/2033 |
| | | | | 604/135 |
| 2013/0190693 | A1* | 7/2013 | Ekman | A61M 5/3202 |
| | | | | 604/192 |
| 2013/0204195 | A1* | 8/2013 | Ekman | A61M 5/326 |
| | | | | 604/197 |
| 2013/0211338 | A1* | 8/2013 | Roberts | A61M 5/3287 |
| | | | | 604/198 |
| 2013/0226085 | A1* | 8/2013 | Roberts | A61M 5/3272 |
| | | | | 604/110 |
| 2013/0245665 | A1* | 9/2013 | Scandurra | A61M 29/02 |
| | | | | 606/194 |
| 2014/0039403 | A1* | 2/2014 | Mercer | A61M 5/326 |
| | | | | 604/191 |
| 2014/0135705 | A1* | 5/2014 | Hourmand | A61M 5/2033 |
| | | | | 604/196 |
| 2014/0180216 | A1* | 6/2014 | Lee | A61M 5/3221 |
| | | | | 604/195 |
| 2014/0207073 | A1* | 7/2014 | Shang | A61M 5/3157 |
| | | | | 604/189 |
| 2014/0221936 | A1* | 8/2014 | Edhouse | A61M 5/326 |
| | | | | 604/198 |
| 2014/0257194 | A1* | 9/2014 | Edhouse | A61M 5/3232 |
| | | | | 604/198 |
| 2014/0378911 | A1* | 12/2014 | Dolk | A61M 5/20 |
| | | | | 604/227 |
| 2015/0051574 | A1* | 2/2015 | Tan | A61M 5/3007 |
| | | | | 604/500 |
| 2015/0320640 | A1* | 11/2015 | Christensen | A61J 1/2096 |
| | | | | 29/428 |
| 2016/0106920 | A1* | 4/2016 | Stefansen | A61M 5/326 |
| | | | | 604/198 |
| 2016/0279343 | A1* | 9/2016 | MacDonald | A61M 5/3156 |
| 2017/0182253 | A1* | 6/2017 | Folk | F16F 9/361 |
| 2017/0196771 | A1* | 7/2017 | Hooven | A61M 5/14244 |
| 2018/0015224 | A1* | 1/2018 | Veilleux | A61M 5/31511 |

OTHER PUBLICATIONS

Callaghan et al. ("Relationship between pulse-wave velocity and arterial elasticity",Medical and Biological Engineering and Computing, 1986, vol. 24, Issue 3, pp. 248-254) (Year: 1986).*
Lange et al. ("Usability of a new disposable autoinjector platform device: results of a formative study conducted with a broad user population", Medical Devices: Evidence and Research 2015:8 255-264) (Year: 2015).*
Written Opinion of the International Searching Authority for International Patent Application No. PCT/US2017/022249, dated May 23, 2017.
International Search Report for International Application No. PCT/US2017/022249, dated May 23, 2017.
European Patent Application No. 20177494, Extended European Search Report, dated Sep. 14, 2020.

* cited by examiner

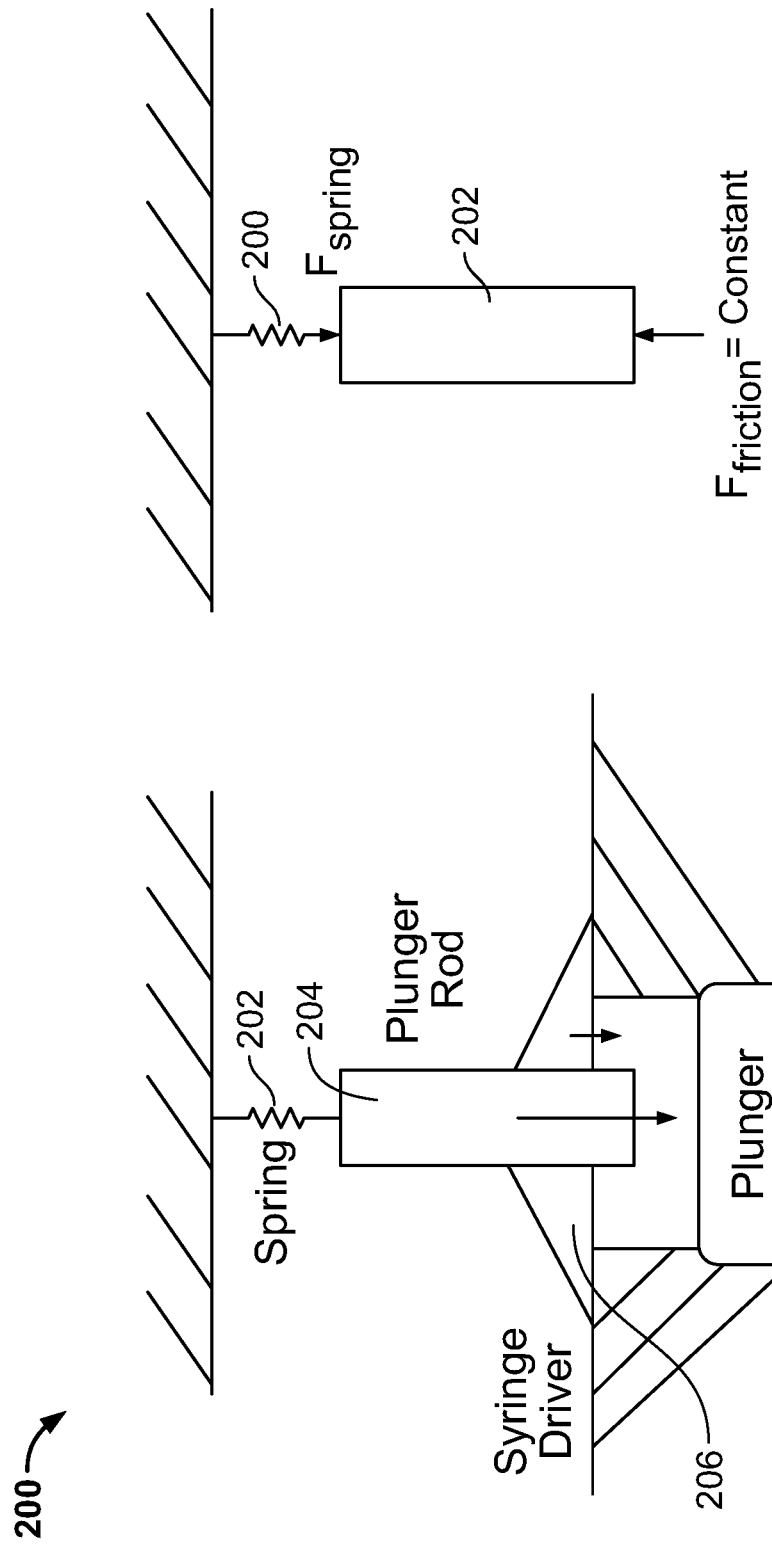

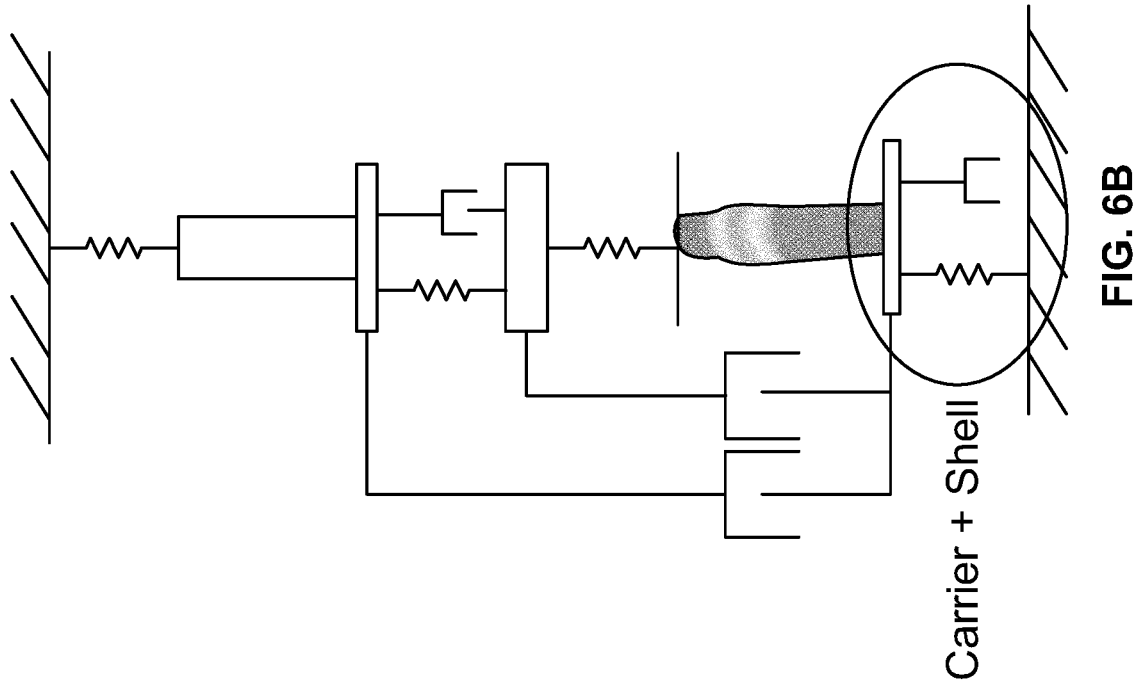
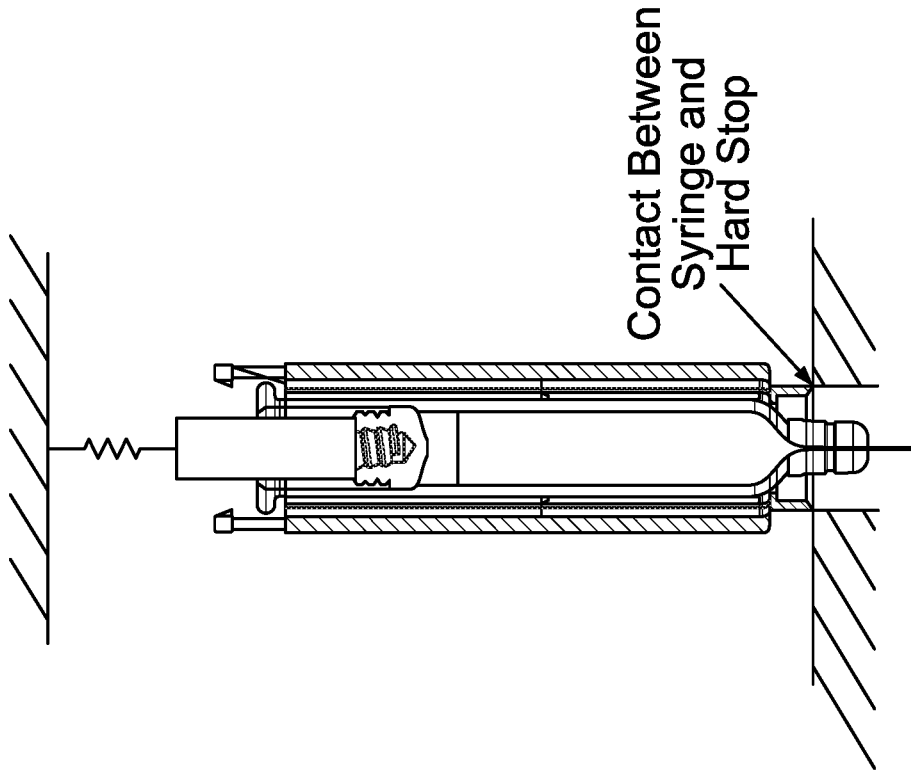
FIG. 6B
FIG. 6A

REDUCING PROBABILITY OF GLASS BREAKAGE IN DRUG DELIVERY DEVICES

CROSS-REFERENCE TO RELATED APPLICATIONS

This is the United States national phase of International Patent Application No. PCT/US2017/022249, filed Mar. 14, 2017, which claims the priority benefit of U.S. Provisional Application No. 62/308,578, filed Mar. 15, 2016, the entire contents of each of which are expressly incorporated herein by reference.

FIELD OF THE DISCLOSURE

The present disclosure relates to injection devices for drug delivery. More particularly, the present disclosure relates to determining the probability of failure of an autoinjector having a certain configuration, and modifying one or several parameters of the autoinjector to improve its reliability.

BACKGROUND

Drug delivery devices, such as autoinjectors, on-body injectors and hand-held injectors, are commonly prescribed for patients to self-administer medication. Such devices typically include a mechanism (e.g., a spring) that operates on a pre-filled syringe in response to a triggering event, such as the patient pressing a button on the device. The mechanism drives the needle into the patient and operates on the plunger to deliver the medication subcutaneously via the needle. These drug delivery devices may be constructed as single-use or reusable devices.

Autoinjectors and on-body injectors offer several benefits in delivery of medication as compared to conventional syringes, such as simplicity of use. However, a mechanism may exert excessive force on a glass syringe, causing breakage. Due to the interaction of multiple parts in a drug delivery device, breakage in general is difficult to predict.

SUMMARY

Disclosed herein are techniques for determining the probable failure rate of a drug delivery device having certain parameters, and using the probable failure rate in designing the drug delivery device. The drug delivery device can be an autoinjector with a mechanism that drives a needle and a plunger of a syringe in order to subcutaneously deliver a drug. As discussed below, a system of this disclosure can apply one or several parameters of an autoinjector (e.g., spring constant), a glass syringe (e.g., mass), and drug product (e.g., fluid density) to a 1D kinematic model of the drug delivery device to generate a prediction of the peak pressure within the glass syringe. The system then can determine, based on the predicted peak pressure and empirical data that relates peak pressure to probability of failure, the probability that the autoinjector under consideration will fail.

One example embodiment of these techniques is a non-transitory computer-readable medium storing instructions. When executed on one or more processors, the instructions implement a method for determining predicted failure rates of drug injection (or "drug delivery") devices. The method includes receiving a set of parameters that specify physical properties of (i) a syringe, and (ii) a liquid drug, and (iii) a drug injection device configured to deliver the liquid drug to a patient via the syringe. The method also includes receiving failure rate data that specifies a measured rate of failure of the drug injection device in response to various peak pressures within the syringe, applying the received set of parameters to a kinematic model of the drug injection device to determine a predicted peak pressure within the syringe, including determining the predicted peak pressure as a function of impact velocity of the liquid drug, and determining a probability of failure of the drug injection device using (i) the received failure rate data and (ii) the predicted peak pressure. The method further includes providing an indication of the determined probability of failure to an output device.

Another example embodiment is a method for manufacturing drug injection devices. The method includes receiving, by one or more processors, a fixed set of parameters that specify physical properties of a syringe and a liquid drug. The method further includes determining a set of parameters that specify physical properties of a drug injection device configured to deliver the liquid drug to a patient via the syringe, including: (i) generating, by the one or more processors, a candidate set of parameters for the drug injection device, (ii) applying, by the one or more processors, the fixed set of parameters and the candidate set of parameters to a kinematic model of the drug injection device to determine a predicted peak pressure within the syringe, including determining the predicted peak pressure as a function of impact velocity of the liquid drug, (iii) determining, by the one or more processors, a probability of failure of the drug injection device using the determined predicted peak pressure, (iv) if the probability of failure is above a threshold value, repeating the steps (i)-(iii) with a modified candidate set of parameters, and (v) selecting the candidate set of parameters if the probability of failure is not above the threshold value. The method further includes manufacturing the drug injection device using the determined set of parameters.

Still another embodiment of these techniques is a drug injection device configured to deliver a liquid drug to a patient via a syringe. The drug injection device is prepared by a process including receiving a fixed set of parameters that specify physical properties of a syringe and a liquid drug, determining a set of parameters that specify physical properties of a drug injection device configured to deliver the liquid drug to a patient via the syringe, and using the determined set of parameters to manufacture the drug injection device. Determining the set of parameters includes (i) generating a candidate set of parameters for the drug injection device, (ii) applying the fixed set of parameters and the candidate set of parameters to a kinematic model of the drug injection device to determine a predicted peak pressure within the syringe, including determining the predicted peak pressure as a function of impact velocity of the liquid drug, (iii) determining a probability of failure of the drug injection device using the determined predicted peak pressure, (iv) if the probability of failure is above a threshold value, repeating the steps (i)-(iii) with a modified candidate set of parameters, and (v) selecting the candidate set of parameters if the probability of failure is not above the threshold value.

BRIEF DESCRIPTION OF THE DRAWINGS

FIG. 4A is a pre-impact kinetic diagram, according to which the system of FIG. 1 can model an autoinjector.

FIG. 4B is a simplified pre-impact kinetic diagram, according to which the system of FIG. 1 can model an autoinjector.

FIG. 6A is a second-impact diagram, according to which the system of FIG. 1 can model an autoinjector.

FIG. 6B is a simplified second-impact diagram, according to which the system of FIG. 1 can model an autoinjector.

Same reference numerals are used in the drawings to identify same or similar elements and structures in the various embodiments.

DETAILED DESCRIPTION

System Overview

Figure 1:
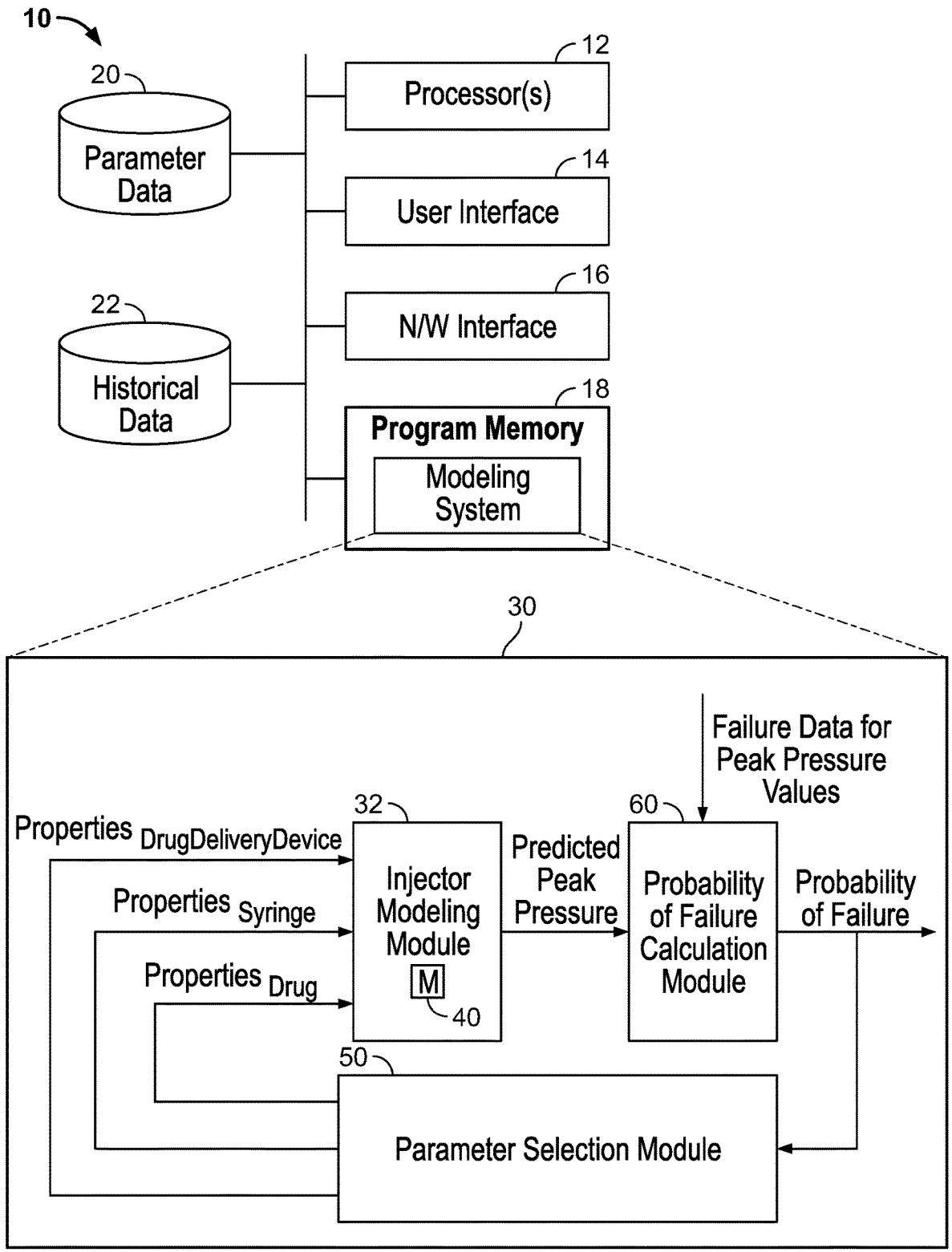
FIG. 1 is a block diagram of an example computing system in which the techniques of the present disclosure can be implemented.

FIG. 1 is a block diagram of an example computing system 10 in which some of the modeling and parameter selection techniques of this disclosure can be implemented.

The computing system 10 can include a single computer, a portable computer, a server or a group of servers. In an example implementation, the computing system 10 includes one or more processors 12 (e.g., CPUs), a user interface 14 (e.g., a touchscreen, a monitor and a keyboard), a network interface 16 configured for wired and/or wireless communications, a non-transitory computer-readable program memory 18, a parameter data storage 20, and a historical data storage 22, interconnected by a communication link such as a digital bus. The program memory 18 can include persistent (e.g., a hard disk) as well as non-persistent (e.g., RAM) components. The storage components 20 and 22 can be implemented in a local or remote memory in accordance with any suitable data storage techniques (e.g., as a relational database).

A modeling system 30 can be stored in the program memory 18 as a set of instructions executable on the one or more processors 12. The modeling system 30 can include an injector modeling module 32 that receives indications of properties of a drug delivery device, a syringe on which the drug delivery device operates, and a drug delivered by the drug delivery device to a patient via the syringe. Using these parameters, the injector modeling module 32 generates a peak pressure prediction within the syringe based on the input in accordance with a kinematic model 40.

An example implementation of the kinematic model 40 is discussed below with reference to FIGS. 4A-6B. Examples of properties the injector modeling module 32 can receive as input are discussed below with reference to various drawings. Potential and/or actual values of these properties can be retrieved from the parameter data storage 20, which in turn can receive these values via the user interface 14 or the network interface 16, from a parameter selection module 50 that can generate candidate values automatically. In various scenarios, the parameters defining input to the injector modeling module 32 can correspond to parameters of existing devices or components or candidate parameters for devices or components being designed.

The modeling system 30 also can include a probability of failure calculation module 60 that receives the peak pressure prediction from the injector modeling module 32 as well as empirical failure data for peak pressure values, which can be stored in the historical data storage 22, for example. The probability of failure calculation module 60 determines a probability of failure using a statistical technique such as the two-term Weibull distribution.

Figure 8:
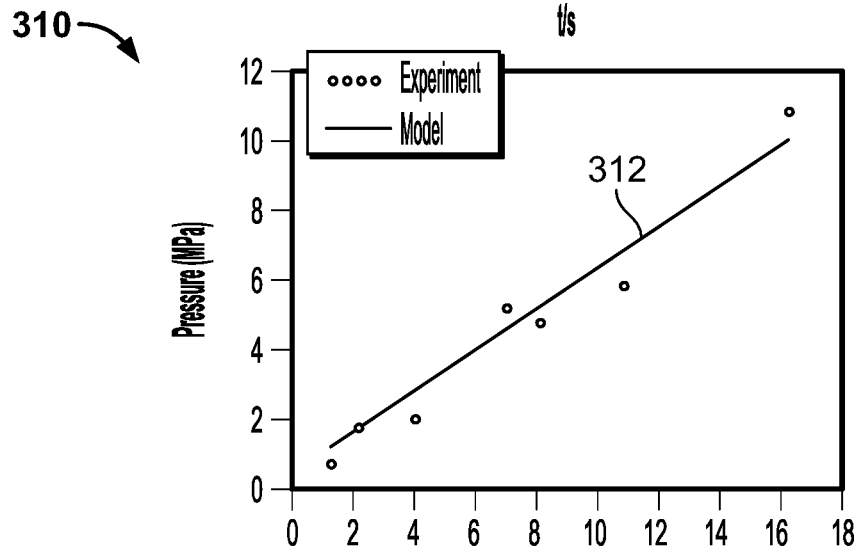
FIG. 8 is a graph that illustrates fitting plunger damping to experimental data, which the system of FIG. 1 can use with a model of an autoinjector.

The probability of failure calculation module 60 can provide an indication of the determined probability to a user via the user interface 14. Moreover, in some implementations, the parameter selection module 50 can use the probability of failure output by the module 34 to select a new set of candidate parameters. As discussed in more detail below with reference to FIG. 8, the parameter selection module 50 can iterate through various candidate values to identify parameters that yield a sufficiently low probability of failure. The parameters then can be used in manufacturing.

If desired, the injector modeling module 32 can be implemented in one server or group of servers, and the parameter selection module 50 can be implemented in another server or group of servers. More generally, the components illustrated in FIG. 1 can be distributed among multiple systems and interconnected in any suitable manner.

Next, an example autoinjector the system of FIG. 1 can model is discussed with reference to FIGS. 2A and 2B. An example succession of operational states of this autoinjector (the "firing sequence") is then discussed with reference to FIGS. 3A-F. It is noted, however, that at least some of the techniques of this disclosure similarly can be applied to other drug delivery devices. For example, drug delivery devices generally suitable for simulation using the techniques of this disclosure can include hand-held injectors.

More generally, the techniques of this disclosure can be applied to devices in which a component that advances a liquid drug (or another liquid) uses coil compression, torsion, or another type of mechanical energy storage. Moreover, these techniques can be applied to non-mechanical systems such as propellant-driven systems.

Example Autoinjector and Firing Sequence

Figure 2A:
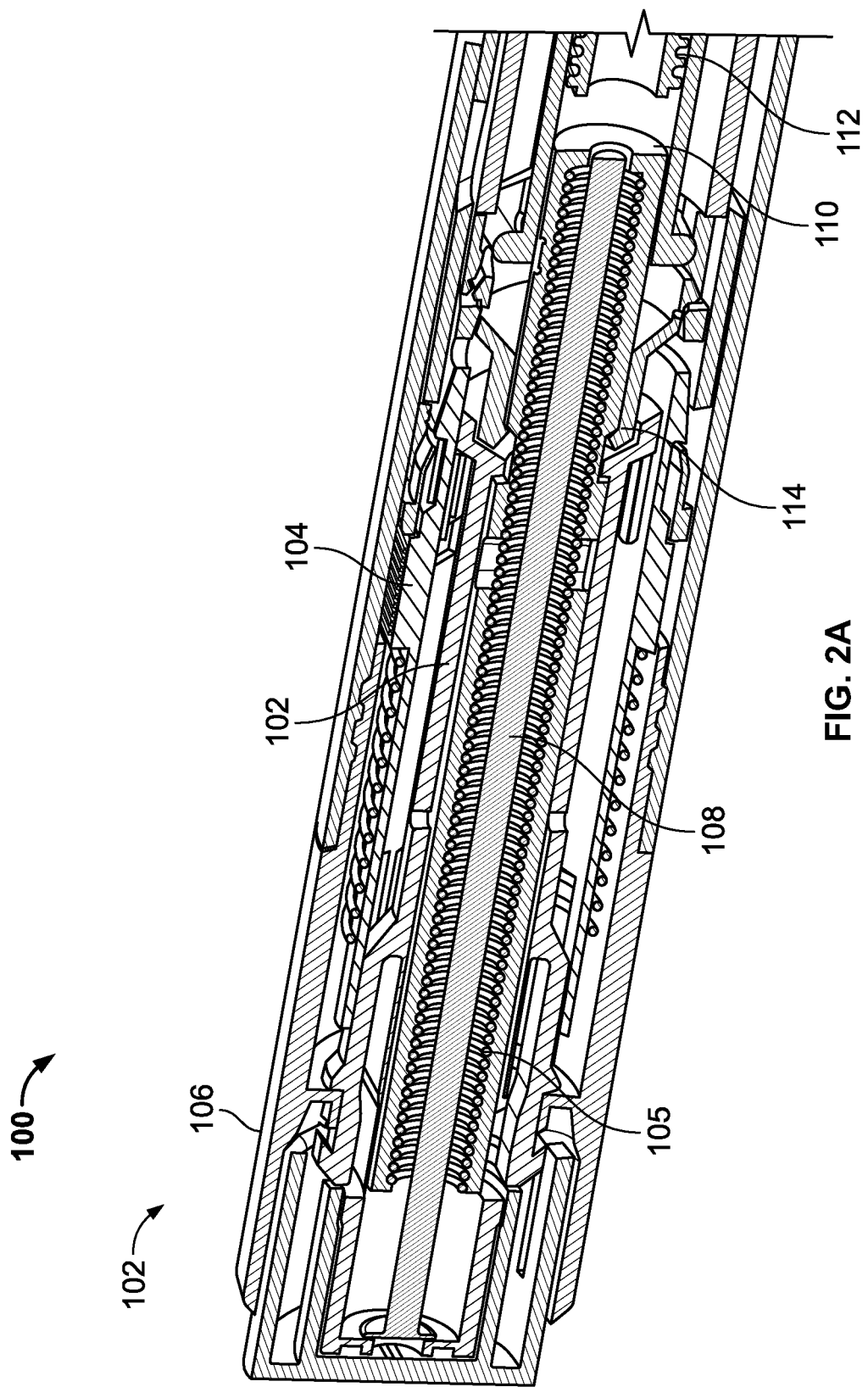
FIG. 2A illustrates a cross-section of a proximal portion of an autoinjector which the system of FIG. 1 can model, in an enlarged perspective view.
Figure 2B:
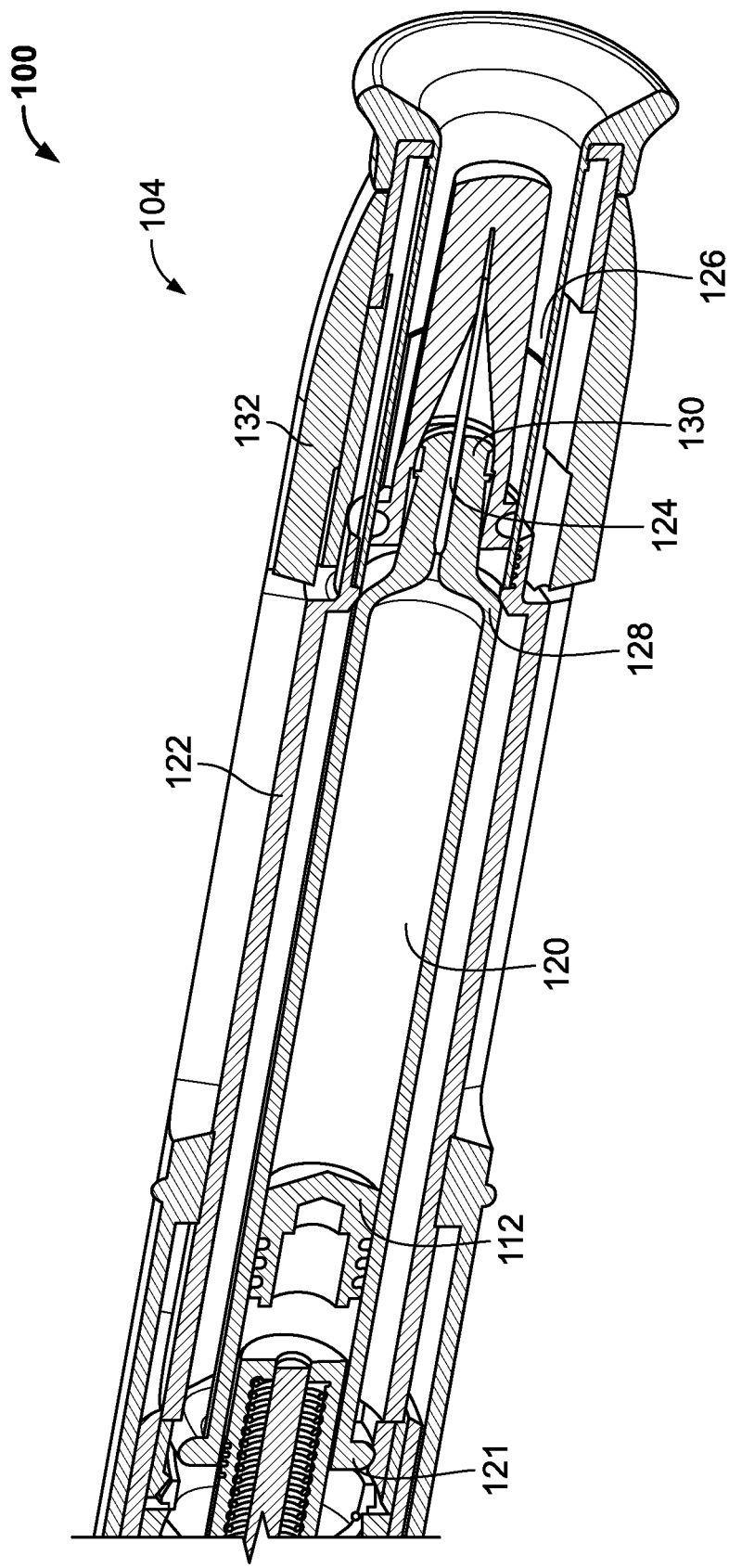
FIG. 2B illustrates a cross-section of a distal portion of the autoinjector of FIG. 2A, in an enlarged perspective view.

An example autoinjector 100 includes a proximal end 102 illustrated in FIG. 2A and a distal end 104 illustrated in FIG. 2B. The autoinjector 100 is of a type for which the modeling system 30 can generate a predicted peak pressure and determine the probability of failure. However, the autoinjector 100 is only one example of a suitable drug delivery device, and the modeling system 30 in general can model glass breakage in a wide variety of devices in which a mechanism exerts a force on a syringe to deliver a drug to a patient. As a more specific example, the modeling system 30 can model glass breakage in a drug delivery device that, unlike the autoinjector 100, does not include the auto-insertion.

The autoinjector 100 can be configured as a pen-type device. Some embodiments of the autoinjector 100 can be configured as a disposable, single use device which delivers a fixed dose of the drug. In other embodiments, the autoinjector 100 may be configured as a reusable device. Reusable drug injection devices 10 may be constructed to deliver a multiple doses of a drug where the doses of the drug may be fixed or user/patient-settable.

Referring first to FIG. 2A, the autoinjector 100 comprises a shell or housing 106, which may be open at the distal end 104 and closed at the proximal end 102. The housing 106 can be constructed as a single, unitary component or constructed from multiple components or sections that are combined into a single, integral unit. The housing can be made of plastic, for example.

The housing 106 encloses an actuator 102 and an actuator sleeve 104. A spring 106 is disposed along a spring guide rod 108 inside a plunger rod 110. As illustrated best in FIG. 2B, a plunger-stopper (or simply "plunger") 112 is positioned on a same virtual axis as the plunger rod 110. Collectively, the components 102-110 can be referred to as the "power pack," as these components store, and release during operation, kinetic energy used by the autoinjector 100. As further illustrated in FIG. 2B, a glass syringe 120 is encased within a syringe carrier 122. The plunger 112 is moveable through the chamber of the syringe 120 to advance a fluid column (i.e., the drug) toward a shoulder 128 and into a needle 124. The portion of the syringe 120 that contains a portion of the needle 124 defines a cone area 130, and the opposite side of the syringe 120 defines a flange 121. A needle shield 126 removeably encloses the cone area 130 and the needle 124 prior to activation of the autoinjector 100. Prior to removal, the needle shield 126 is within a front shell 132, which is a portion of the housing 106.

In operation, the patient removes the needle shield 120, places the autoinjector 100 against her skin, and depresses the activation button (not shown) or otherwise initiates operation of the autoinjector 100. The actuator 102 releases the energy of the compressed spring 106. In response, the spring 106 drives the plunger rod 110, which in turn advances the plunger 112 and the syringe driver 114.

Analysis of the autoinjector 100 using high-speed video have revealed that two events impart significant impact forces to the syringe. The first event is occurs when the moving plunger rod 100 comes in contact with the stationary plunger 112 upon initial activation of the autoinjector 100. The second impact event occurs when the moving syringe carrier 122 contacts the stationary front shell 132 and the end of needle extension. The forces of these two impacts can break glass at low occurrence rates. If the plunger 112 is placed lower in the syringe 120, the first impact becomes more important, i.e., more likely to be the cause of breakage. Here, plunger depth refers to distance between the top of the flange 121 to the top of the plunger 120. Accordingly, "higher" refers to the plunger 120 being closer to the flange 121, and "lower" refers to the plunger 120 being farther away from the flange 121 and closer to the needle 124.

More particularly, when the plunger rod 110 strikes the plunger 112, an impact is generated. The load generates pressure waves that propagate through the fluid column. For the combination of materials and geometries typical of glass syringes, a pressure wave will "couple" to the glass barrel as it propagates axially. This coupling results in a reduction of wave speed, and radial motion of the syringe 120. The coupled wave oscillates through the syringe 120.

After the plunger rod 110 impacts the plunger 112, the plunger rod 110, the syringe 120, and the syringe carrier 122 advance together. This motion inserts the needle 124 into the patient. A second impact load is generated when the syringe carrier 122 impacts the internal stop on the shell 132. The second impact produces a second pressure wave that radiates through the same components. Both the plunger rod 110 strike against the plunger 112 and the syringe carrier 122 strike against the front shell 132 produce similar pressure waves. The pressure wave results in a local stress that in low occurrences may result in fracturing of the glass syringe 120.

FIGS. 3A-E illustrate an example firing sequence of an autoinjector. For convenience, the sequence is discussed with reference to the autoinjector 100 of FIGS. 2A and 2B. The firing sequence can take several milliseconds to complete.

Figure 3A:
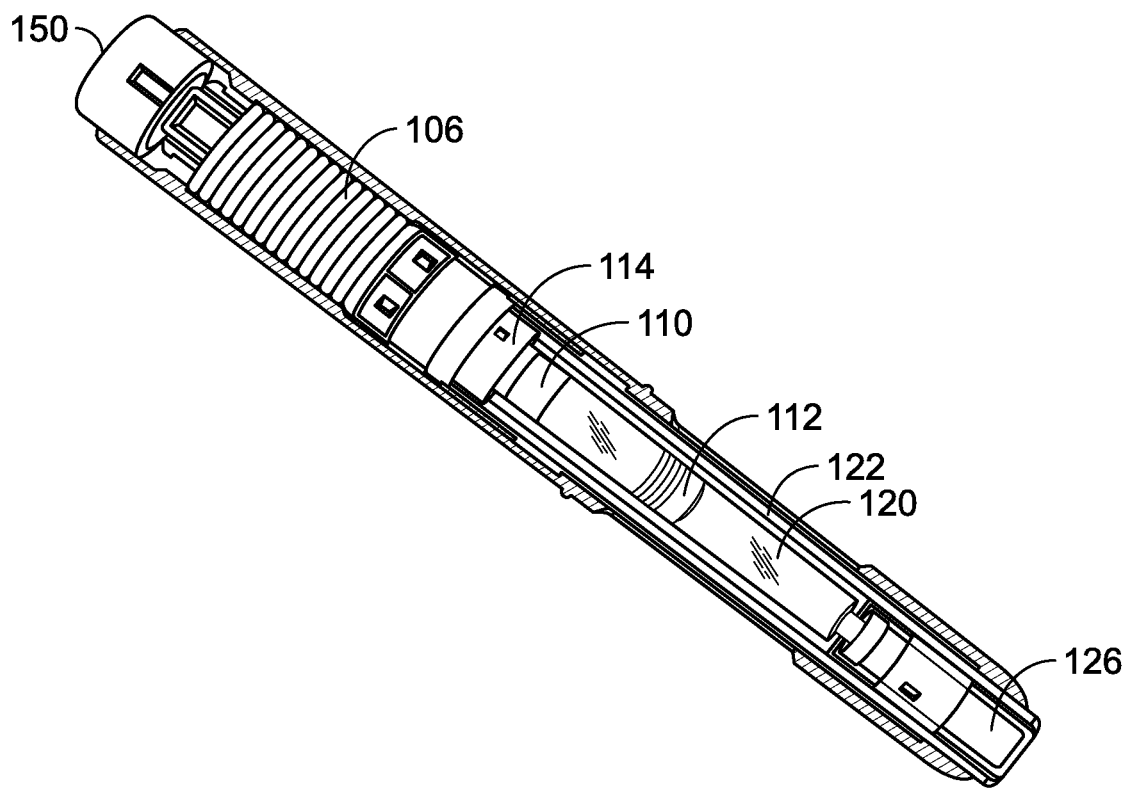
FIG. 3A illustrates an example autoinjector which the system of FIG. 1 can model, prior to initiating of a firing sequence.

FIG. 3A illustrates the autoinjector 100 prior to the initiation of the firing sequence. The autoinjector 100 is loaded with the glass syringe 100, pre-filled with a liquid drug. At this stage, the needle shield 126 covers the needle 124. The spring 106 has not been actuated.

Figure 3B:
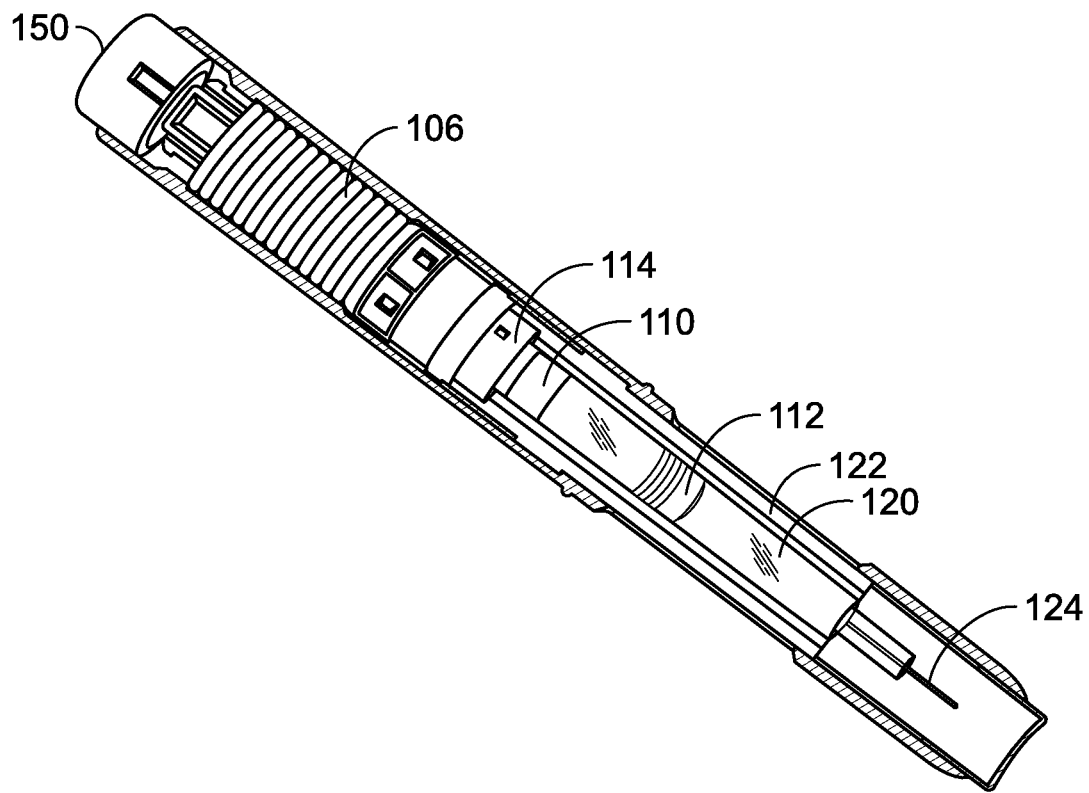
FIG. 3B illustrates the autoinjector of FIG. 3A at the first stage of the firing sequence, where a needle shield is removed.
Figure 3C:
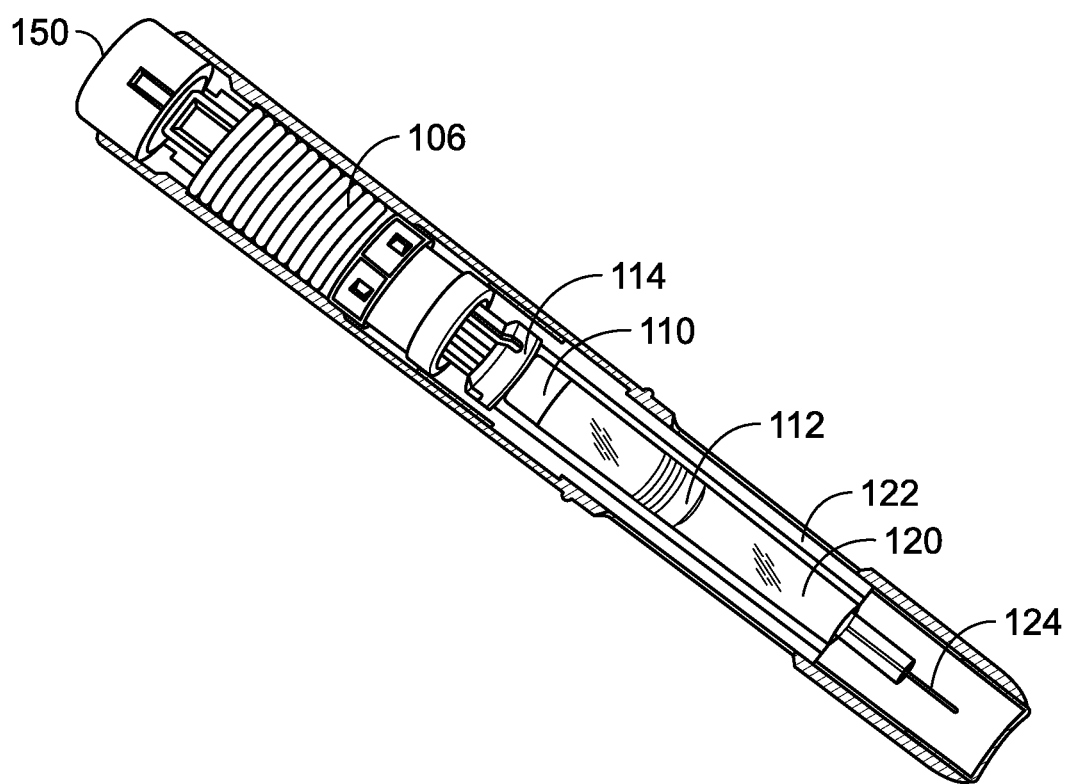
FIG. 3C illustrates the autoinjector of FIG. 3A at the second stage of the firing sequence, where a patient presses the button to cause a spring to advance a plunger rod and a syringe driver.

At the stage depicted in FIG. 3B, the patient removes the needle shield 126, exposing the needle 124. The patient then patient presses a button to activate the device (FIG. 3C). As a result, the spring 106 acts upon the plunger rod 110 and the syringe driver 114. In response, the plunger rod 110 along with the syringe driver 114 starts to advance in the direction of the needle 124. In this example implementation, the syringe driver 114 advances with the plunger rod 112 due to interference fit.

Figure 3D:
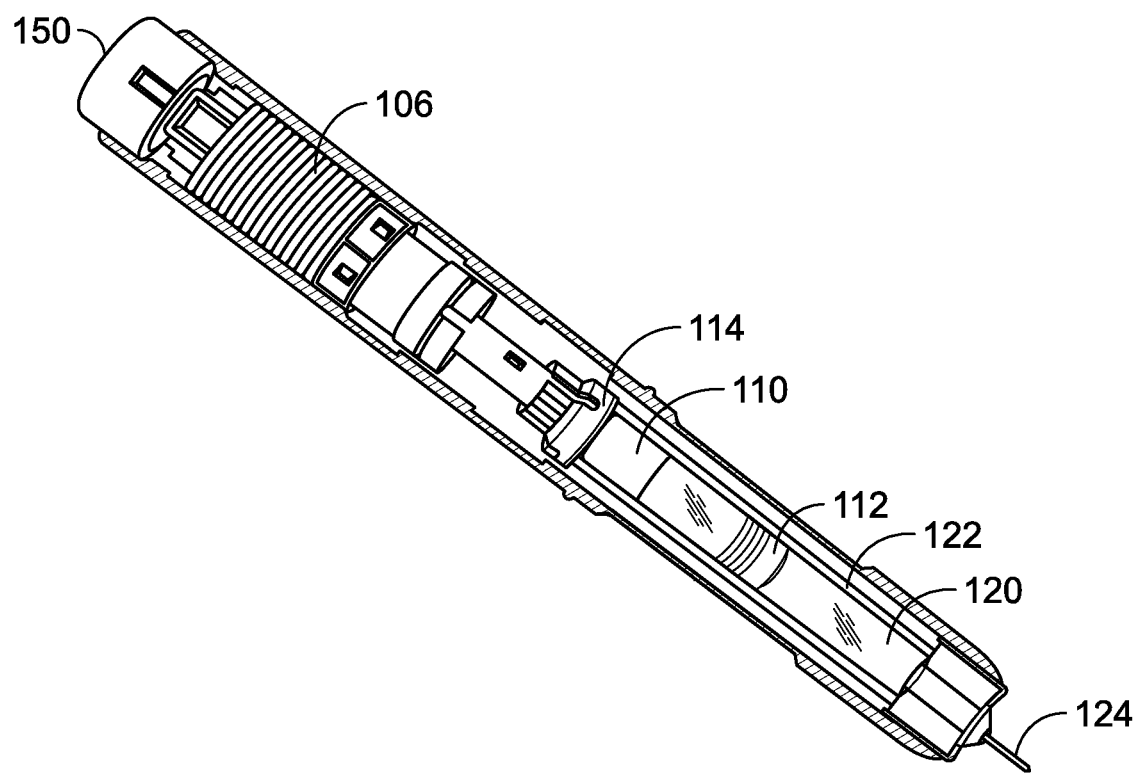
FIG. 3D illustrates the autoinjector of FIG. 3A at the third stage of the firing sequence, where the syringe driver advances the needle into the patient.

Next, at the stage of FIG. 3D, the plunger rod 110 along with the syringe driver 114, the syringe 120, and the syringe carrier 122 starts to advance in the direction of the point on the patient's body where the drug is to be administered. The plunger rod 110 and the syringe driver 114 advance sufficiently far to drive the needle 124 into the skin. After this step, the syringe driver 114 no longer advances at the same rate as the plunger rod 110.

Figure 3E:
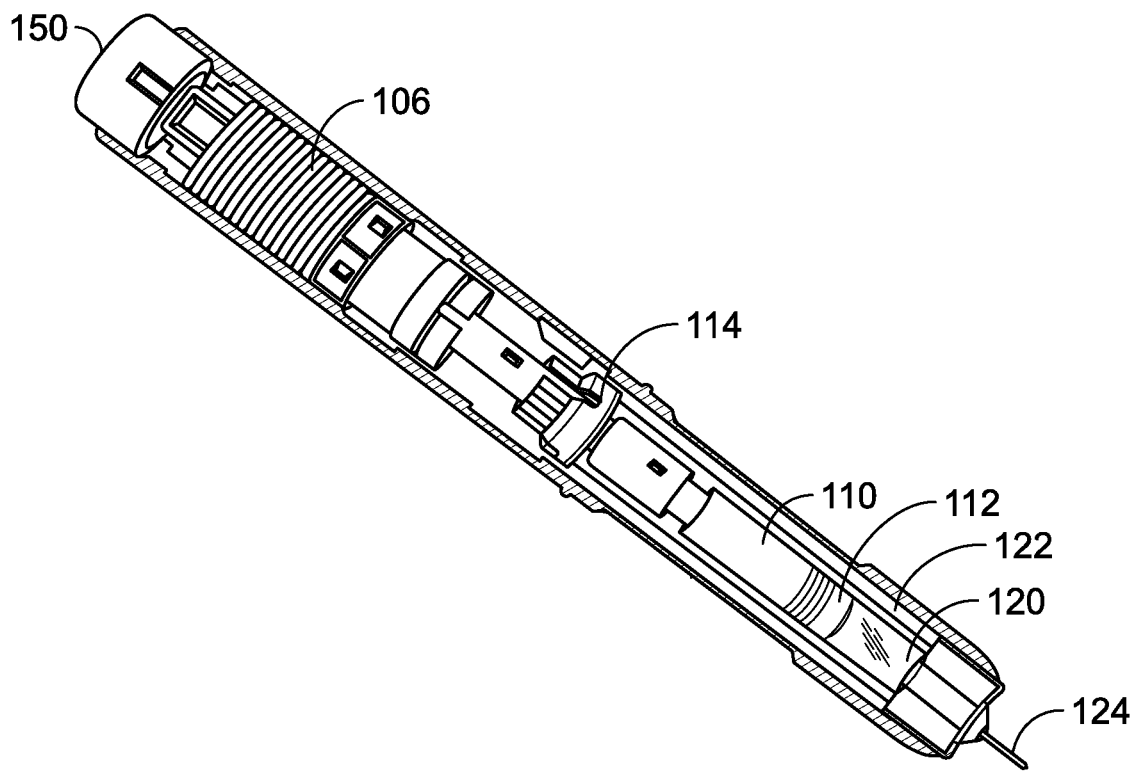
FIG. 3E illustrates the autoinjector of FIG. 3A at the fourth stage of the firing sequence, where the plunger rod disengages the syringe driver and advances to the plunger.
Figure 3F:
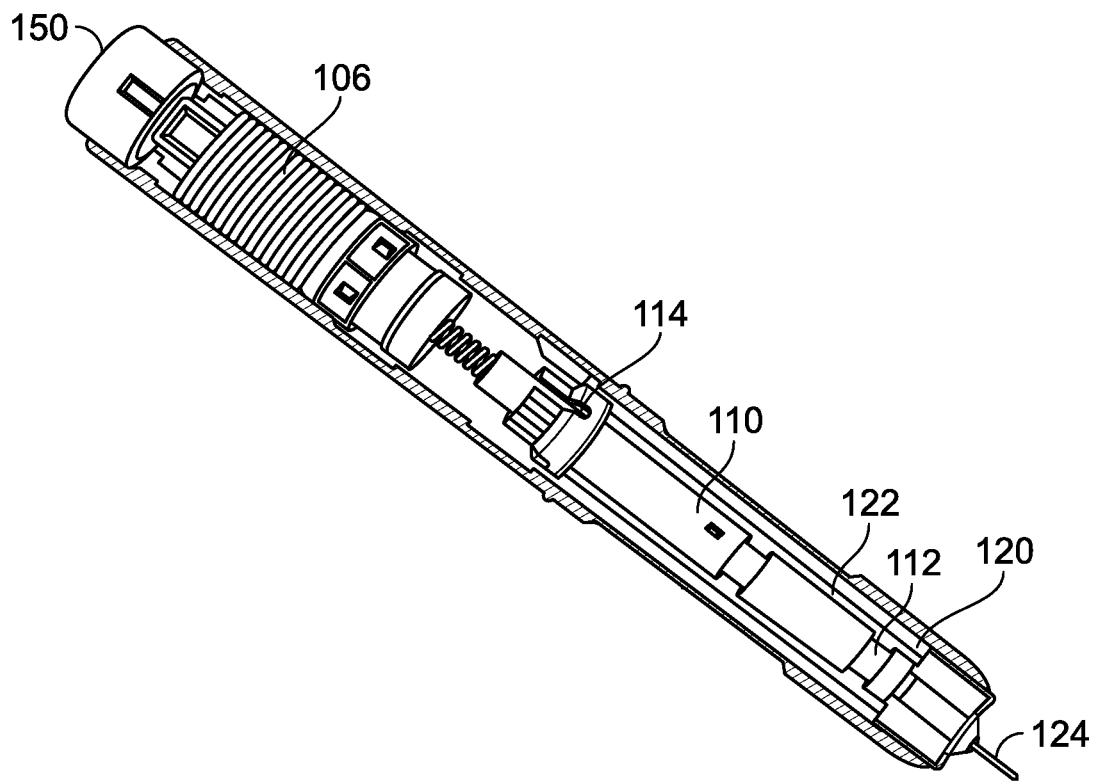
FIG. 3F illustrates the autoinjector of FIG. 3A at the fifth, last stage of the firing sequence, where the plunger extrudes the drug from the syringe.

Now referring to FIG. 3E, the plunger rod 110 at this point disengages the syringe driver 114 and advances to impact the plunger 112, which begins to extrude the drug out of the syringe 120. The plunger 112 then extrudes the drug from the syringe 120 via the needle 11, as illustrated in FIG. 3F.

In the sequence of FIGS. 3A-F, the plunger rod 110 does not make contact with the plunger 112 before the syringe driver 114 causes the syringe 120 to advance. In another sequence according to which the autoinjector 100 can operate, the plunger rod 110 releases form the syringe driver 114 early in the sequence. The plunger rod 110 then impacts the plunger 112 before the syringe 120 and the needle 124 are driven into the patient. As indicated above, the impact of the plunger rod 110 on the plunger 112 is referred to in the discussion of modeling as the "first impact," and the event corresponding to the syringe carrier 114 coming to a stop at the end of the travel is referred to as the "second impact."

In an example implementation of an autoinjector 100, it has been observed that the plunger rod 110 moves forward slowly over a small distance (e.g., approximately 2 mm) upon activation. Subsequently, the autoinjector 100 fully releases the plunger rod 110, and the model enters a pre-impact period. At this time, the syringe carrier 122 also moves forward (e.g., travelling approximately 0.4-1.2 mm).

1D Kinematic Model

Referring back to FIG. 1, the model 40 can be used to model behavior of drug delivery devices such as the autoinjector 100 discussed above. Generally speaking, the model 40 is based on conservation of momentum, with the spring 106 discussed above being the driving force. The model 40 uses a set of 1D force-balance equations to predict pressure history within the barrel of the syringe 120 and determine dynamic responses of the components of the autoinjector 100 as a function of time. More particularly, the model 40 describes the kinematics of the autoinjector 100 and can be used to calculate the timing and magnitude of the pressure waves generated within the syringe. To this end, the model 40 uses the Korteweg equation to predict peak pressure as a function of impact velocities. As discussed in more detail below, the model 40 models acoustics using method of characteristics (a technique for solving partial differential equations), with the addition of a unique boundary condition. The model 40 thus can capture the fluid-structure interaction between the glass of the syringe and drug product, which otherwise is difficult to model.

Some of the activation parameters of the model 40 can be developed high-speed cameras to capture velocities of the moving components of an autoinjector similar to the autoinjector 100. The masses of the individual components of the autoinjector 100 can be measured using conventional techniques. The spring constant(s) can be measured statically. The geometric dimensions of the components of the autoinjector 100 can be obtained using schematics or lab measurements. Further, the model 40 can be validated using experimental data mapped to inputs and outputs to the model 40.

The spring 106 is modeled as a linear spring with an equilibrium length. For the purposes of the model 40, only the overall dynamics of the plunger 112 are important, and the plunger 112 is represented by a spring and a parallel dashpot. The fluid column (i.e., the drug product) in the device is modeled as an acoustic media, which interacts with the glass syringe through fluid-structure interactions. High-speed video analysis has shown that very small amounts of drug product were extruded during activation of the autoinjector. To model this pressure release, the needle end of the fluid column was modeled with a combination of acoustic theory and Hagen-Poiseuille theory. Much like the plunger, the interaction of the syringe with the carrier/front shell is modeled as a parallel spring and dashpot.

The output of the 1D kinematic model is peak pressure at the end of the needle (where, according to empirical data, breakage occurs). These peak pressures can be separated into the peak pressures associated with first and second impact.

The model 40 is based on several assumptions. These assumptions are based on experimental testing, and/or high-speed video analysis, and/or known theoretical approaches.

As an initial matter, the model 40 is based on the observation that 2D and 3D effects are not significant (based on experiments with 2D and 3D models, which exhibit similar behavior to 1D model within the syringe). Further, the model 40 can operate according to the assumption that glass breakage is independent of method of pressure generation. Still further, the model 40 can rely on peak dynamic pressure to predict glass breakage.

Simplifications related to fluid properties and flow can include the following: Hagen-Poiseuille flow develops instantaneously in needle; drug product is modeled as Newtonian fluid; pressure wave phenomena are approximated through method characteristics 1D shock tube solution; speed of sound in the drug product is equivalent to water; flow through the barrel acts as a 1D plug flow; and peak pressure in the barrel drives stress in the funnel. Simplifications related to the spring can include the following: the spring and the overall actuation component act as an ideal linear spring with one source of damping; damping originates from the syringe driver which is approximated through a dry friction model; spring acts as a free spring contributing ⅓ of its mass dynamically; and spring dynamic and static force behavior are equivalent. Simplifications related to elasticity and viscosity can include the following: plunger-stopper acts as Voigt visco-elastic model; plunger elasticity behaves non-linearly; plunger dynamic and static elasticity is equivalent; plunger viscosity behaves linearly; conservation of momentum applies instantaneously to the top portion of the plunger upon impact; and the syringe and the syringe carrier do not move independently of one another. Other simplifications can include the following: air gap, when present, compresses adiabatically; cavitation and air bubbles provide negligible damping effect; cavitation is not significant for glass breakage; and patient skin is modeled as rigid body.

Experiments have shown that an air gap can be present between the fluid column (i.e., the drug) and the plunger 112, when the autoinjector 100 is held vertically. In a horizontal orientation, which sometimes is used to deliver the drug, the air forms a bubble that can move within the syringe 120. This air gap can reduce the peak pressure substantially only when it is large (e.g., several mm in diameter); otherwise, the air gap can reduce peak pressure only marginally. Because the orientation of the autoinjector 100 cannot be assumed, and because of the other simplifications and/or assumptions listed above, the air gap is not used in the model 40. In other embodiments of the injector modeling module 32, however, the air gap can be explicitly accounted for.

Next, the model 40 is discussed in detail with reference to the diagrams of FIGS. 4A-6B.

To more clearly distinguish between idealized elements and their counterparts in an example implementation of the autoinjector 100, the components of a modeled autoinjector are illustrated using different reference numbers. Thus, FIG. 4A illustrates a pre-impact kinetic diagram of a system 200 that includes a spring 202 rigidly fixed at one end and coupled to a plunger rod 204 at the other end. The plunger rod 204 is in an interference fit with a syringe driver 206. The plunger rod 204 is moveable toward a plunger 208 as the spring 202 decompresses.

Input parameters for the model 40, and the corresponding notation, are summarized below in the next subsection. In addition to these inputs, the discussion below uses the following notation: $x_{object}$ refers to the position of an object, $x_{object}^o$ refers to the initial position of an object, $u_{object}$ refers to velocity of an object, $u_{object}^o$ refers to the initial velocity of an object, $P_{atm}$ refers to the atmospheric pressure, $H = x_{meniscus}^o\,0 - x_{plunger}^o\,0$ refers the initial height of the air gap, $A_{barrel} = \pi D_{barrel}^2/4$ refers to the cross-sectional area of syringe interior, x refers to position in syringe, P(x, t) refers to pressure in syringe, u(x, t) refers to velocity in syringe, a refers to Kortaweg wave speed, and $R = D_{barrel}/2$ refers to the inner radius of syringe.

After activation, the model 400 separates the system 200 into two components. The first component is the plunger rod 204 and the spring 202, which includes the effective mass for the spring 202. In an idealized spring-mass system (spring of constant mass per unit length), the linear velocity of the spring 202 is accounted for by lumping ⅓ of the total spring mass into the mass:

$$M_{rod+spring} = M_{rod} + \frac{M_{spring}}{3} \tag{1}$$

The second component includes the remaining components besides the shell of the device (autoinjector):

$$M_{carrier\_assembly} = M_{plunger} + M_{syringe} + M_{fluid} + M_{carrier} \tag{2}$$

As illustrated in FIG. 4B, two forces act on the plunger rod 204 and syringe components. A spring force pushes on the plunger rod-spring component, and a frictional force (transmitted through the syringe driver) connects the plunger rod 204 with the rest of the autoinjector. The dynamic friction force is assumed to be a constant. In an example embodiment, the dynamic friction force is experimentally determined to have the values between 3 and 10N. The spring law is linear with equilibrium lengths of 13-18 cm and spring constants of 150-500 N/m, in an example embodiment. The equilibrium length and the spring constant of course depend on the spring type and individual variations. First, the spring plastically deforms a significant amount when placed into the component of the autoinjector responsible for driving the syringe (see FIG. 2A), and second, measuring the spring force within the autoinjector automatically accounts for extra internal friction not present in a bare-spring system.

Applying Newton's law, F=ma, to the two component leads to equations of motions (3) and (5) illustrated below. The initial conditions, illustrated in equations 6-9, state that both masses begin to rest with known positions. In the equations below, over dots denote derivatives with respect to time.

$$M_{rod+spring}\ddot{x}_{rod+spring} = F_{spring} - F_{friction} \tag{3}$$

$$F_{spring} = -k(x_{rod+spring} - L) \tag{4}$$

$$M_{carrier\_assembly}\ddot{x}_{carrier\_assembly} = F_{friction} \tag{5}$$

$$x_{rod+spring}(t=0) = x_{rod+spring}^0 \tag{6}$$

$$x_{carrier\_assembly}(t=0) = x_{carrier\_assembly}^0 \tag{7}$$

$$\dot{x}_{rod+spring}(t=0) = 0 \tag{8}$$

$$\dot{x}_{carrier\_assembly}(t=0) = 0 \tag{9}$$

The initial positions for the plunger rod 204, the spring 202, and carrier assembly account for the initial rod and plunger depths as well as the device activation travel distances. The initial velocities are assumed negligible. These equations are linear and have an analytic solution:

$$x_{rod+spring}(t) = \left[x_{rod+spring}^0 - \left(L - \frac{F_{friction}}{k}\right)\right]\cos\left(\sqrt{\frac{k}{M_{rod+spring}}}\,t\right) + \left(L - \frac{F_{friction}}{k}\right) \tag{10}$$

$$x_{carrier\_assembly}(t) = \frac{F_{friction}}{2M_{carrier\_assembly}}t^2 + x_{carrier\_assembly}^0 \tag{11}$$

The impact time is found by equating the positions of the plunger rod 204 and plunger 208 and solving for the impact time. Equation (12) is a non-linear equation for $t_{impact}$, substituting equations (10) and (11) for the respective terms:

$$x_{rod+spring}(t_{impact}) = x_{carrier\_assembly}(t_{impact}) \tag{12}$$

To solve this non-linear equation iteratively, a reasonable initial value for the impact time is required. The frictional force is smaller than the spring force, so the carrier assembly only translated a small amount before the first impact. Thus, a good initial value for the impact time can be found by assuming that the $t^2$ term in equation (12), after expanding the right-hand side with equation (11), is negligible. Equation (5) then can be solved exactly, with the form illustrated in equation (13):

$$t_{impact} \approx \sqrt{\frac{M_{rod+spring}}{k}} \cos^{-1}\left[\frac{x_{carrier\_assembly}^0 - \left(L - \frac{F_{friction}}{k}\right)}{x_{rod+spring}^0 - \left(L - \frac{F_{friction}}{k}\right)}\right] \tag{13}$$

Using equation (13) as an initial estimate, Newton's method can be used to solve equation (12) numerically. The output of the pre-impact simulation are the impact time along with the component positions and velocities at impact:

$$x_{rod}(t_{impact}) \tag{14}$$

$$x_{rod+spring}(t_{impact}) \tag{15}$$

$$x_{carrier\_assembly}(t_{impact}) \tag{16}$$

$$x_{carrier\_assembly}(t_{impact}) \tag{17}$$

Figure 5B:
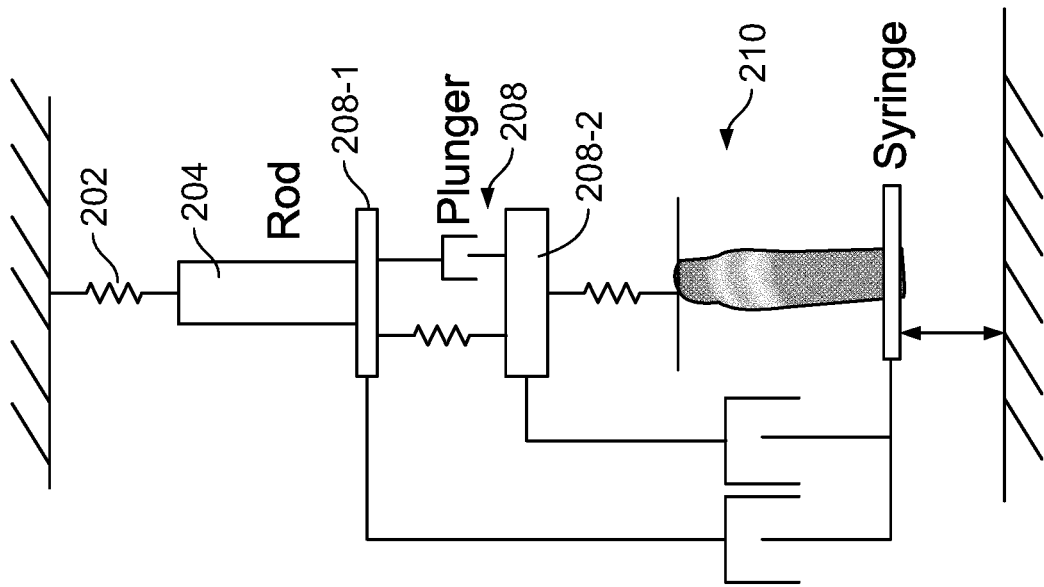
FIG. 5B is a simplified first-impact kinetic diagram, according to which the system of FIG. 1 can model an autoinjector.
Figure 5A:
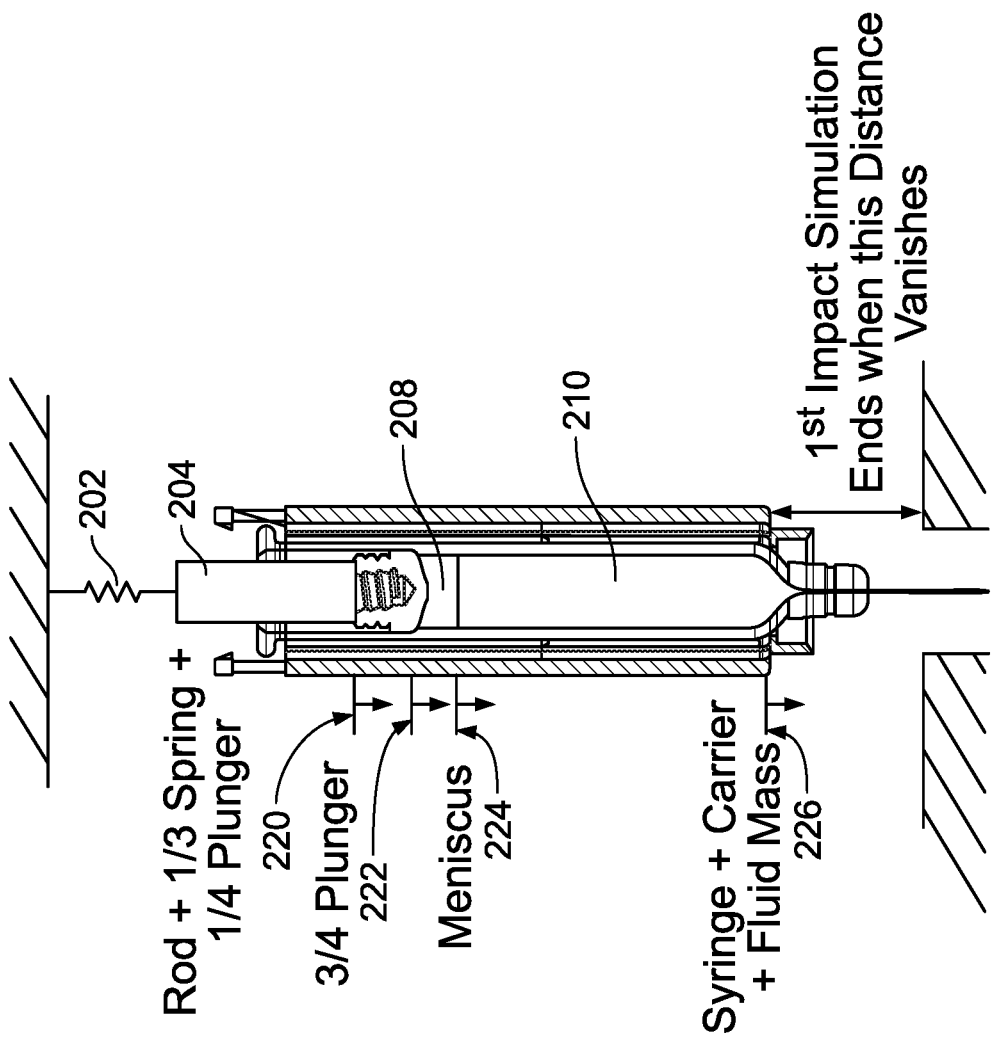
FIG. 5A is a first-impact kinetic diagram, according to which the system of FIG. 1 can model an autoinjector.

Now referring to FIG. 5A, the first impact occurs when the rod 204 impacts the plunger 208. FIG. 5B illustrates conceptual separation of a syringe 210 into four components at this pre-impact stage. The plunger rod 204 can be assumed to impact inelastically with the top of the plunger 208-1, which is assumed to contain ¼ of the mass of the plunger 208. The remaining mass (component 208-2) is assigned to the syringe 210. Throughout the first and second impact, it can be assumed that the plunger rod 204 remains in contact with the top of the plunger 208-1, and that the syringe 210 and the syringe carrier move together at all times. Four positions can be tracked in this system, as illustrated in FIG.

5A: the plunger rod button/plunger top (220), the plunger bottom (222), the top of the meniscus (224), and the bottom of the syringe 210 (226).

Figure 5C:
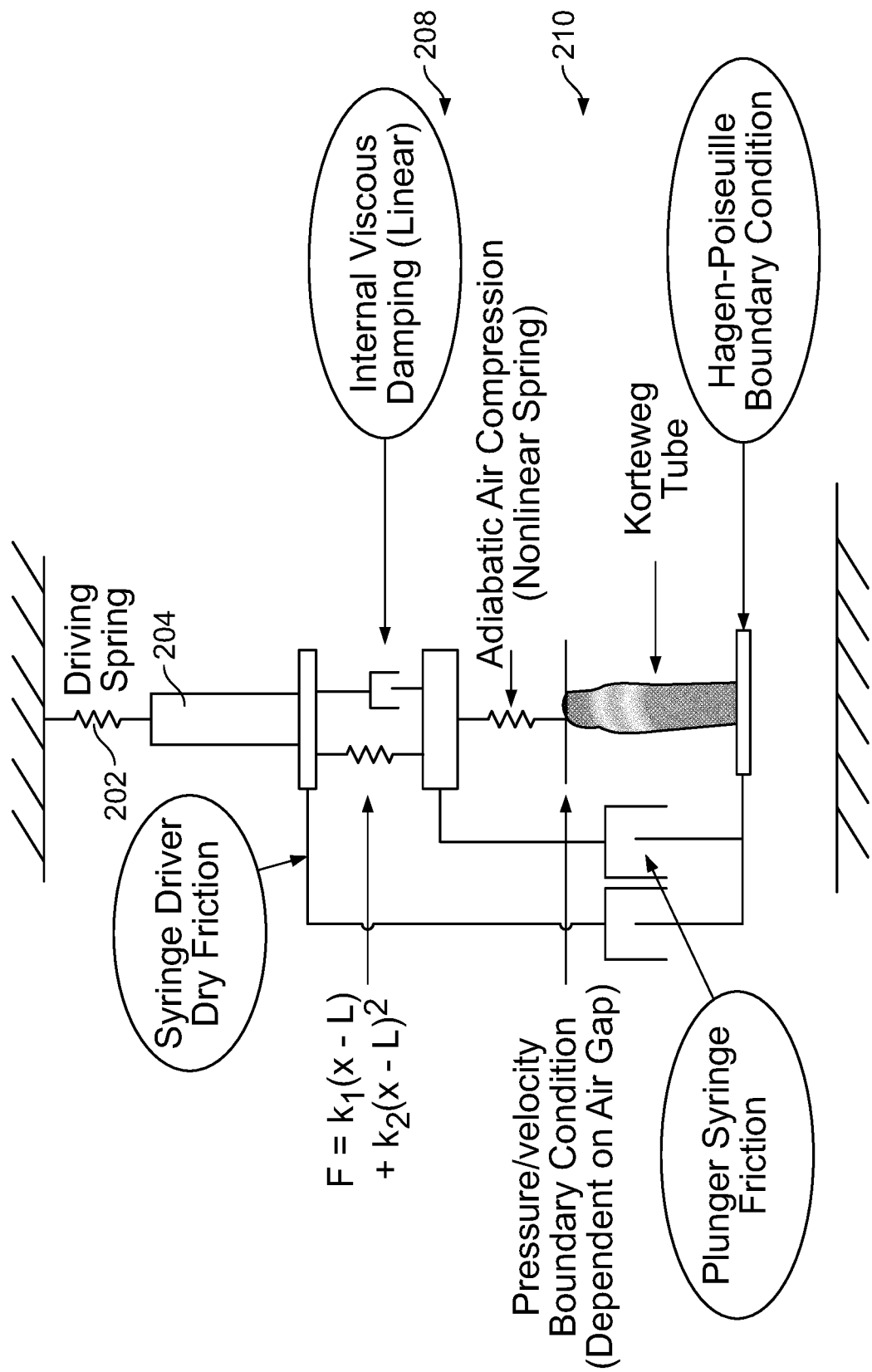
FIG. 5C is an extended first-impact kinetic diagram with boundary conditions, according to which the system of FIG. 1 can model an autoinjector.

With the exception of the shock tube between meniscus and the syringe 210, the forces in the system can be modeled with springs and dashpots, as illustrated in FIG. 5C.

Damping forces are circled in FIG. 5C, and spring forces are not circled. The spring and syringe driver dry friction forces are the same as in the previous model, with the dry friction resisting motion between the syringe driver and plunger rod. The internal forces in the syringe 210 are modeled as a Voigt elastic. The damping is linear, but the spring force, which can be measured experimentally, can be non-linear. The spring 202 is modeled by including a quadratic term to the standard linear spring with an equilibrium length. The plunger 208 interacts with the syringe 210 through direct contact as well as a thin layer of oil, and the interaction is modeled as a linear damping term. When the air gap is included, it is modeled as a spring using an adiabatic compression approximation. The fluid in the syringe 210 is modeled using the Korteweg equations discussed below, along with appropriate boundary conditions.

With continued reference to FIG. 5C, the resulting forces in the system are as follows, with velocities denoted with u:

$$F_{srping} = k(L - x_{rod}) \tag{18}$$

$$F_{syringe\_driver\_damping} = \text{sign}(u_{rod} - u_{syringe})F_{friction} \tag{19}$$

$$F_{plunger\_spring} = \tag{20}$$
$$k_1(x_{plunger} - x_{srod} - L_{plunger}) - k_2(x_{plunger} - x_{rod} - L_{plunger})^2$$

$$F_{plunger\_damping} = C_{plunger}(u_{rod} - u_{plunger}) \tag{21}$$

$$F_{syringe\_friction} = C_{syringe}(u_{syringe} - u_{plunger}) \tag{22}$$

$$P_{air\_gap} = P_{atm}\left(\frac{H}{x_{mensicus} - x_{plunger}}\right)^{\gamma} \tag{23}$$

$$F_{air\_gap} = P_{air\_gap} A_{barrel} \tag{24}$$

$$F_{shock\_tube} = (P_{shock\_tube}(\text{needle\_end}) - P_{atm})A_{barrel} \tag{25}$$

The forces are converted into equations of motion using Newton's law, F=ma, once again:

$$(M_{rod} + \tfrac{1}{3}M_{spring} + \tfrac{1}{4}M_{plunger})\ddot{x}_{rod} = F_{spring} - F_{syringe\_driver\_damping} - F_{plunger\_spring} - F_{plunger\_damping} \tag{26}$$

$$\tfrac{3}{4}M_{plunger}\ddot{x}_{plunger} = F_{plunger\_spring} + F_{plunger\_damping} - F_{plunger\_friction} - F_{air\_gap} \tag{27}$$

$$u_{meniscus} = u_{shock\_tube}(\text{plunger\_end}) \tag{28}$$

$$(M_{syringe} + M_{carrier} + M_{fluid})\ddot{x}_{syringe} = F_{syringe\_driver\_damping} + F_{plunger\_friction} + F_{shock\_pressure} \tag{29}$$

The initial conditions are specified by applying conservation of momentum to the pre-impact output, per equations (14)-(17). The model also can be run without an air gap. In this case, $F_{air\_gap}$ is replaced with equation (30):

$$F_{plunger\_shock} = P_{shock\_tube}(\text{plunger\_end})A_{barrel} \tag{30}$$

The fluid pressure in the syringe 210 can be modeled with one-dimensional Korteweg equation, with tracks pressure and velocity as functions of axial distance and time:

$$\frac{\partial P}{\partial t} = -\rho a^2 \frac{\partial u}{\partial x} \tag{31}$$

$$\frac{\partial u}{\partial t} = -\frac{1}{\rho}\frac{\partial P}{\partial x} \tag{32}$$

Equations (31) and (32) can be solved with the method of characteristics. The wave speed, a, is calculated with the Korteweg equation (33). The wave speed depends on the speed of sound, densities, and geometries of the fluid and solid systems, as illustrated in equation (34).

$$a = \frac{c_{fluid}}{\sqrt{1+\beta}} \tag{33}$$

$$\beta = \left(\frac{c_{fluid}}{c_{solid}}\right)^2 \left(\frac{\rho_{fluid}}{\rho_{solid}}\right)\left(\frac{2R}{h}\right) \tag{34}$$

The tube is broken into N equal elements of size Δx. A time step then can be selected based on the wave speed and step size.

$$\Delta t = \frac{\Delta x}{a} \tag{35}$$

At the start of the first impact, the velocity at every node is set to the syringe velocity output by the pre-impact model of FIGS. 4A and 4B. The pressure is set to atmospheric pressure. At each subsequent time step, interior notes (excluding the nodes near the plunger and the needle) are updated with equations (36) and (37):

$$P(x, t + \Delta t) = \tag{36}$$
$$\frac{1}{2}(P(x - \Delta t, t) + P(x + \Delta t, t)) + \frac{\rho a}{2}(u(x - \Delta t, t) - u(x + \Delta t, t))$$

$$u(x, t + \Delta t) = \tag{37}$$
$$\frac{1}{2\rho a}(P(x - \Delta t, t) + P(x + \Delta t, t)) + \frac{1}{2}(u(x - \Delta t, t) + u(x + \Delta t, t))$$

Two possible boundary conditions exist near the needle. In both cases, the boundary node is updated with equation (38):

$$\frac{P(0, t + \Delta t)}{\rho a} - u(0, t + \Delta t) = \frac{P(\Delta x, t)}{\rho a} - u(\Delta x, t) \tag{38}$$

In both cases, the right-hand side of the equation is known at the start of the time step. If the air gap is present, P(0, t+Δt) is set as the air gap pressure, and the equation is used to solve for the unknown velocity. If there is no air gap, the velocity on the left-hand side is specified as the plunger bottom velocity, and the equation solves for the unknown pressure.

The equation at the needle end is more involved because some fluid is expelled through the needle. There are two unknowns at the start of a time step: u and P at the needle boundary, so two equations are required. The first equation comes from the method of characteristics:

$$\frac{P(L, t+\Delta t)}{\rho a} + u(L, t+\Delta t) = \frac{P(L-\Delta x, t)}{\rho a} - u(L-\Delta x, t) \quad (39)$$

The right-hand side is known, while the unknowns appear on the left-hand side. The remaining equation is derived by assuming P and u follow the Hagen-Poiseuille law:

$$u(L, t+\Delta t)A_{barrel} = u_{syringe}A_{barrel} + \frac{\pi D_{needle}^4}{128\,\mu L_{needle}}(P(L, t+\Delta t) - P_{atm}) \quad (40)$$

Solving both equations simultaneously allows for the update of u and P at the needle boundary. The syringe velocity appears because the extrusion volume is based on the difference in velocity between the average velocity in the shock tube and the velocity of the syringe.

Now referring to FIG. 6A, the second impact is when the carrier contacts a small ledge inside the shell. The equations are identical to first impact besides the addition of two new forces, which are circled with an oval in FIG. 6B.

The impact force between the shell and syringe/carrier is modeled with a linear Voigt viscoelastic element. These extra forces are applied to the syringe:

$$F_{shell\_carrier\_spring} = k_{shell\_carrier}(x_{syringe} - x_{shell}) \quad (41)$$

$$F_{shell\_carrier\_damping} = C_{shell\_carrier}u_{syringe} \quad (42)$$

Inputs to the 1D Kinematic Model

Generally speaking, the model 40 discussed above can receive parameters that specify physical properties of the syringe 120 or 210, the autoinjector 100 or 200, and the drug with which the syringe 120 or 210 is pre-filled. These parameters can relate to geometry, friction, mass, viscosity, elasticity, etc. Some of these input parameters are listed below. In some embodiments, additional parameters can be used or, conversely, some of the parameters listed below can be omitted. More particularly, in some scenarios, only subsets of the parameters listed below can be received, and the remaining parameters can be fixed at certain constant values or eliminated from the model, depending on the embodiment.

Geometric inputs can include some or all of plunger depth, plunger rod wall thickness, plunger rod activation length, syringe barrel diameter ($D_{barrel}$), syringe wall thickness (h), fluid volume ($V_{fluid}$), syringe carrier activation length, plunger rod depth, length of the guide rod, length of guide rod base, length of needle insertion, needle length ($L_{needle}$), needle diameter ($DM_{needle}$), un-sprung length of spring (L). Input parameters related to mass of various components can include one or more of mass of syringe carrier ($M_{carrier}$), mass of pre-filled syringe with drug ($M_{fluid} + M_{syringe}$), mass of plunger, which also may be referred as "plunger-stopper" ($M_{plunger}$), mass of rod ($M_{rod}$), mass of spring ($M_{spring}$). Visco-elastic input parameters can include plunger elasticity parameters ($k_1$ and $k_2$), plunger plasticity ($C_{plunger}$), plunger-syringe viscous damping ($C_{syringe\_friction}$), front shell elasticity ($k_{shell\_carrier}$), and front shell damping ($C_{shell\_carrier}$). Fluid-structure interaction (FSI) input parameters can include one or more of fluid sound speed ($c_{fluid}$), solid sound speed ($c_{solid}$), fluid viscosity ($\mu$), fluid density ($\rho$), solid density for glass ($\rho_{solid}$). Other parameters can include syringe driver friction ($F_{friction}$) and spring constant (k).

Alternative Modeling Techniques

As one alternative to the techniques discussed above, a 2D axisymmetric model can be constructed, approximating the fluid as an acoustic media in contact with the syringe through a fluid-structure interaction. The solid components can be modeled as linear elastics with an additional viscous components. Another alternative is a 3D model does not account for fluid in the syringe. Experimentation has shown that these 2D and 3D models produce similar results.

However, these large-scale models are not as useful as predictive tools. One reason is, as a result of numerical issues, the models only converge at low-impact speeds. Long simulation times restrict device exploration in two different device configurations. Further, the models consistently predict that the syringe should break in the should region, whereas empirical data shows that the breakage events tend to originate in the cone region.

Moreover, the results for 2D and 3D modeling are heavily dependent on the penalty parameter used in the contact regions. This parameter is an unphysical numeric value used to keep computational regions from interpenetrating. Dependence on the results on the penalty parameter indicates that the contact boundary conditions are not captured accurately. Also, these models predict extremely high glass stress that would shatter most syringes. The empirical data does not support these predictions.

Nevertheless, 2D and 3D modeling supports the theory that tensile stresses in the glass, which cause failure, are created by the pressure waves in the fluid column, that an acoustic model is a suitable approximation for the fluid column, and that a detailed plunger dynamics have an insignificant effect on the pressure waves.

As one alternative to the techniques discussed below, a Finite Element Method (FEM) can be used to predict peak stress in structural elements during impact. However, FEM techniques carry an inherent error and tend to generate a large amount of numerical noise. Moreover, FEM approaches are computationally expensive. Experiments have shown that, when implemented on a laptop, the system of FIG. 1 takes only several minutes to model the interaction between an autoinjector, a syringe, and a drug to determine the probability of failure, whereas modeling this interaction using a suitable FEM approach takes hours.

In contrast, the speed at which the modeling techniques of this disclosure can be executed facilitate the use of Monte Carlo simulation. Generally speaking, Monte Carlo simulation is a powerful technique for examining the variability of outputs for a given set of inputs with known variation. Although it is theoretically possible to run Monte Carlo simulations with an FEM technique, this approach is impractical, as Monte Carlo simulations are prone to difficulties with converging across a wide range of inputs.

It is also noted that the model 40 predicts peak pressure in the syringe, which can be directly measured to drive the model 40 to accuracy, whereas a typical FEM predicts stress. Stress is an inferred property, and as such cannot be measured directly.

Application of Experimental Data to Models

In an embodiment, the model 40 uses several damping constants that are derived from experimental (empirical) data. For example, high-speed video capturing techniques can be used to measure rod velocity, syringe velocity, pressure, etc. at multiple times for a certain autoinjector. The experiments can be repeated multiple times to generate a reliable data sample. The system 10 then can store the data sample in the historical database 22, for example (see FIG. 1). Subsequently, the system 10 can utilize parameters derived from experimental data to model autoinjectors that share some of the properties of the actual autoinjector. In an example embodiment, the model 40 uses the following damping constants: (i) syringe driver friction, which is the friction between the syringe driver and the plunger rod, (ii) internal plunger damping, (iii) plunger-syringe friction, and (iv) the shell damping constant.

Figure 7:
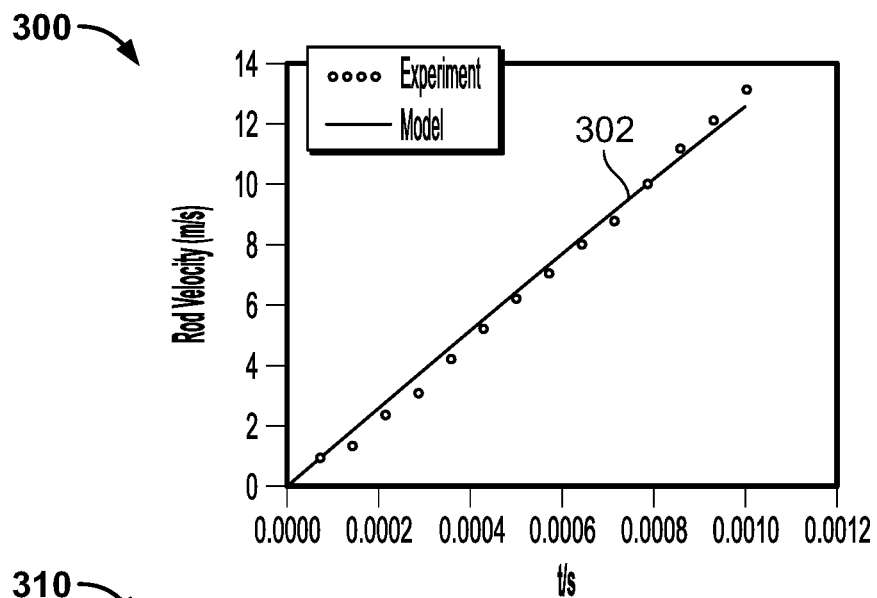
FIG. 7 is a graph that illustrates fitting syringe driver friction to experimental data, which the system of FIG. 1 can use with a model of an autoinjector.

Referring to FIG. 7, the power pack of a certain actual autoinjector can be tested without a syringe, a syringe carrier, a front shell, etc. to produce a graph 300, in which data points illustrate measurements of rod velocity as a function of time (the "velocity trace"). In this example, the plot is an average of ten runs. The velocity trace then can be compared with the analytical predictions of the pre-impact model (see FIGS. 4A and 4B), and the plunger syringe friction can be fit with least squares. In FIG. 7, line 302 illustrates the theoretical prediction after fitting the syringe driver friction. Syringe driver friction can be evaluated for each individual spring/power pack combination, as the this parameter can vary significantly across different configurations of an autoinjector.

After fitting the pre-impact model, internal plunger damping and plunger-syringe friction appear in the first-impact model (see FIGS. 5A-5C) as new parameters. To fit internal plunger damping, peak first-impact pressure can be measured over a range of impact velocities. As illustrated in graph 310 of FIG. 8, the relationship is approximately linear over a wide range of impact velocities. Experiments show that the air gap between the plunger and meniscus has a relatively weak effect on the peak pressure measurements. In the air gap model, the singularity in the adiabatic approximation can cause an unrealistically large peak pressure and a nonlinear relationship between impact speed and pressure, as the actual impact causes air to entrain within the drug. Accordingly, the air gap can be removed from all simulations used to predict peak pressures. This results in a more physically accurate simplification. A least squares fit 312 can be used to determine plunger damping.

Figure 9:
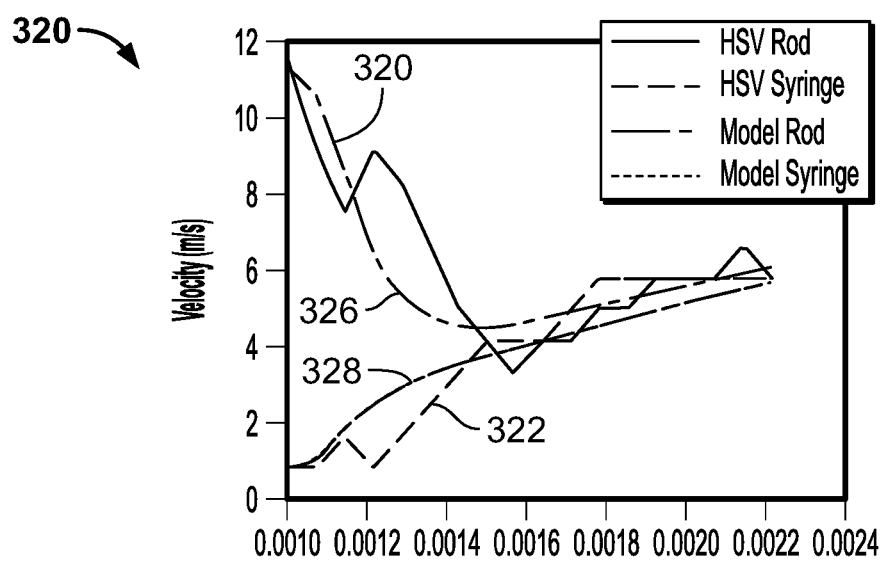
FIG. 9 is a graph that illustrates fitting plunger-syringe friction to experimental data, which the system of FIG. 1 can use with a model of an autoinjector.
Figure 10:
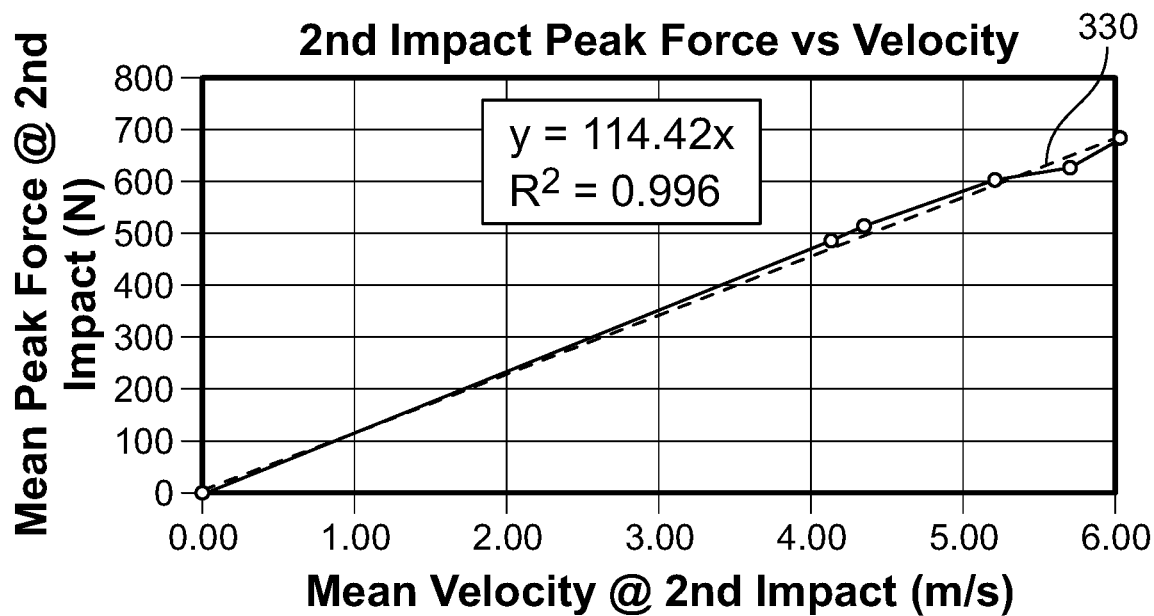
FIG. 10 is a graph that illustrates experimental data indicative of peak measured force on a syringe carrier as a function of impact velocity, which the system of FIG. 1 can use with a model of an autoinjector.

Regarding plunger-syringe friction, this parameter is heavily dependent on the syringe siliconization and individual plunger configuration. As illustrated in FIG. 9, this parameter can be fit by comparing high-speed video traces of the rod 320 and syringe velocity 322 immediately after first impact but before second impact. The model rod and model syringe curves are 326 and 328, respectively. Although the air gap has a negligible impact on the peak pressure, it tends to have a strong effect on the velocity trace after first impact. Thus, an air gap can be reintroduced for this series of simulations. The plunger-syringe friction can be fit, manually or automatically, to the data in graph 320.

Finally, the shell damping constant can be derived from second-impact measurements. In the model 40, the second impact peak force is directly related to the impact velocity with proportionality constant equivalent to the shell damping constant. Thus, the damping constant can be read off the slope of line 330 in FIG. 1, which illustrates the relationship between peak force and impact velocity.

In an example embodiment, the parameter selection module 50 automatically determines the damping constants (i)-(iv) using experimental data stored in the historical database 22 and stores the results in the parameter database 20. In other embodiments, some or all of the damping constants (i)-(iv) can be determined separately and input into the model 40 via user interface controls provided by the parameter selection module 50. For example, an operator can choose to input some of the values manually.

Using Models in Monte Carlo Simulations

As discussed above, the main outputs of the model 40 are the peak pressures experienced at the first and second impacts for the various configurations of interest. Monte Carlo simulations can be conducted to predict both the average peak pressures as well as the ranges likely to be seen in the field, i.e., when the autoinjector being modeled is manufactured.

Figure 11:
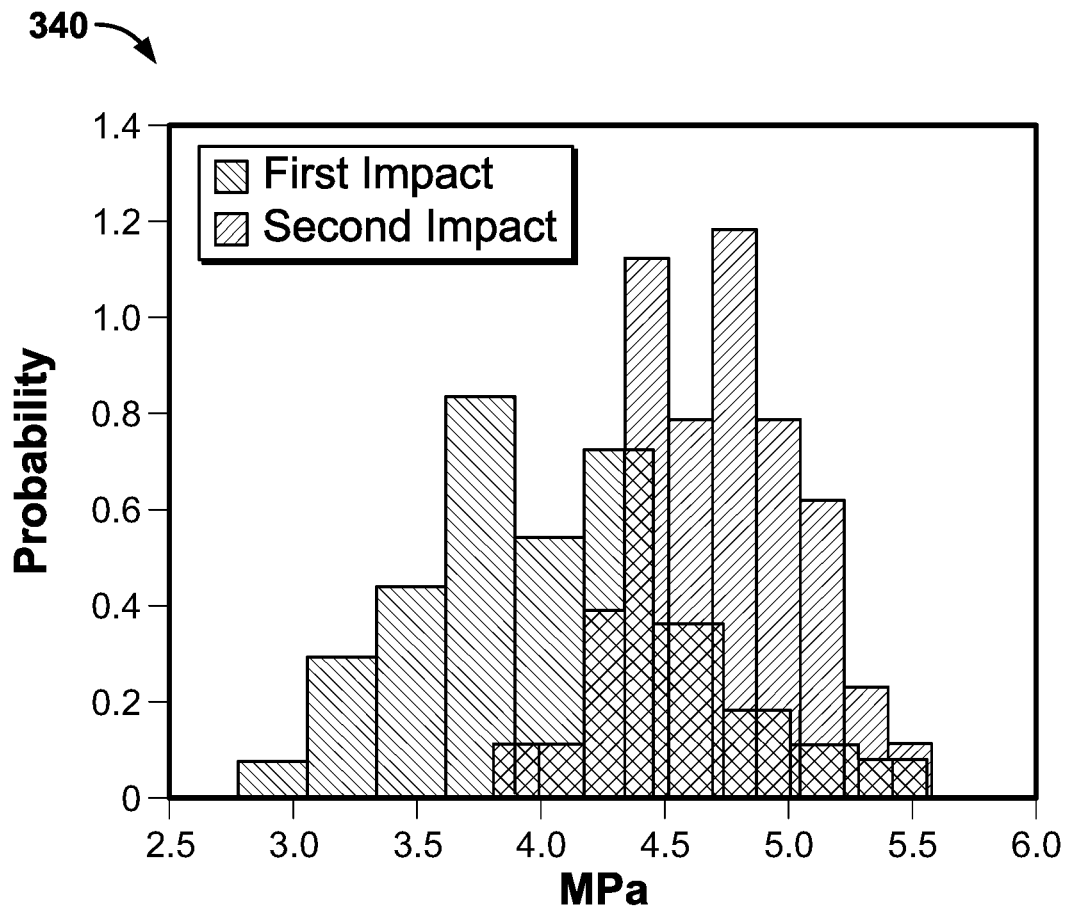
FIG. 11 illustrates predicted distributions of peak pressures, which the system of FIG. 1 can generate using a model.

There are four steps in a general Monte Carlo simulation: (i) a domain of possible inputs is defined (in these simulations, the inputs are spring forces, plunger depth, etc.); (ii) inputs are generated randomly from a probability distribution (in these simulations, a normal random variable with a measured mean and standard deviation for each input parameter is used), (iii) deterministic computations are run for all generated input sets; and (iv) the results are aggregates of peak pressures for the first and second impacts. For each candidate configuration, average values can be measured for every input parameter, and standard deviations can be measured or approximated. In each simulation, parameters can be drawn from normal distributions with corresponding means and standard deviations. A sample distribution 340 is illustrated in FIG. 11. This distribution is based on the model 40 producing one hundred independent simulations, in each of which a peak pressure was recorded. For this simulation, a nominal plunger depth of 10.5 mm was used.

The same distribution 340 illustrates that, first, average peak pressure is significantly higher for second impact at the plunger depths selected for the simulation. Second, the standard deviation for the first impact peak pressure is higher than second impact. Experimentation shows that this is chiefly a result of the power pack variability. Finally, the distributions can be reasonably approximated as normal, so each distribution can be accurately specified using the mean and standard deviation. Multiple experiments have been conducted, and all Monte Carlo simulations showed similarly normal distributions.

Using Models with Taguchi Methods

Another possible application of the model 40 discussed above is using a two-level Taguchi method to explore the design space of the range of autoinjectors. Taguchi is a specific form of a Design of Experiments methodology used to identify the strongest influencing variables in a multivariable space (Design of Experiments is a set of methods used to identify experimental selection and sequence to maximize the value of information generated). A high and low value can be identified for a subset of the input variables. A set of N simulations can be designed, such that every pair of parameters is combined in all four possible ways (low-low, low-high, high-low, and high-high).

The peak pressures can be modeled for all N simulations. Based on the results, a signal-to-noise (SNR) value can be calculated for each experiment. For each parameter, the average value of the SNR can be calculated separately for the simulations with a low parameter value and the simulations with a high parameter value. The difference ($\Delta$) between SNR values (the low set of simulations compared with the high set of simulations) indicates the significance of each parameter on the peak pressures. Larger absolute values for $\Delta$ are associated with more important parameters.

For example, after N runs, the output of a Taguchi method for the model 40 can be a first $\Delta$ value for the spring constant, generated for the first impact, and a second Δ value for the spring constant, generated for the second impact. For an example configuration of an autoinjector being modeled, relatively large Δ values for the spring constant indicate that the spring constant is a significant parameter for the first impact as well as the second impact. However, a first Δ value and a second Δ value can be similarly produced for the spring length parameter for the first impact and the second impact, respectively, and a relatively small first Δ value can indicate that the spring length is not a significant parameter for the first impact but is a significant parameter for the second impact. As yet another example, a first Δ value and a second Δ value can be produced for the parameter specifying the rod activation distance. Both the first Δ value and the second Δ value can be relatively small, indicating that this parameter is not significant for either the first impact or the second impact.

Referring back to FIG. 1, the modeling system 30 can provide appropriate UI controls for selecting N, specifying parameters for Taguchi method runs, displaying and tabulating the Δ values, etc. The modeling system 30 can implement the Taguchi functionality in the parameter selection module 50, for example.

Glass Breakage Impact Characterization

The probability of failure calculation module 60 can use the two-term Weibull distribution because this approaches yields more accurate predictions, particularly at the end of the "long tail." This is especially useful when modeling autoinjectors that tend to deliver high-viscosity drugs. However, in other implementations other techniques can be used, such as using a logistic fit function, a log-logistic fit function, a spline fit function, or a Gaussian fit function.

Generally speaking, glass breakage occurs when stress is applied to a critical surface defect size on the glass. The term "defect" here refers to a micro-scale geometric variation that meets manufacturing specification, and is generally not detectable by current production methods. Needle cone surfaces are free-formed, and thus these defects are inherent to syringe formation. The origination of the glass fracture occurs where the largest stress is applied to the largest surface flaw. This can be referred to as the "weakest link" phenomena. The stress in the glass can be expressed by the relationship in equation (43):

$$\delta = K_c \times P \tag{43}$$

Example data collected from a characterization study shows behavior indicative of an exponential rise followed by an exponential decay with the inflection point at a certain breakage probability (e.g., 50%). This observation and the "weakest link" phenomena basis for glass fracture lead to a Weibull two parameter distribution fit to the data following equation (44):

$$P_f = 1 - \exp\left(-\left(\frac{\delta}{\delta_0}\right)^m\right) \tag{44}$$

The probability of glass breakage ($P_f$) is a function of local stress (σ), surface geometry ($\sigma_O$), and glass surface quality (m). This approach uses peak pressure as a surrogate for stress since stress cannot be measured directly within the syringe. Equation (43) demonstrates that stress is directly proportional to pressure (P) assuming a random distribution of surface flaws with concentration factor ($K_c$).

The probability of failure calculation module 60 then can extrapolate the fit to the observed pressures delivered by the drug delivery device and use the extrapolated fit to predict probability of glass breakage with different configurations of the drug delivery device. For example, the probability of failure calculation module 60 can predict probabilities of glass breakage within the syringe 120 (see FIGS. 2A-3F) for different sets of parameters of the autoinjector 100, such as the spring constant, the mass of the syringe, the density of the drug, etc.

In an embodiment, the estimation in the glass breakage prediction uncertainty is divided into three components: (i) statistical sampling uncertainty (based on a percent of the absolute value), (ii) measurement uncertainly (based on a percent of the absolute value), and (iii) fit bias compared to actual field data (based on low and high bias). The fit bias can be based purely on the absolute value difference between the prediction and the field-reported value.

Example Methods

Figure 12:
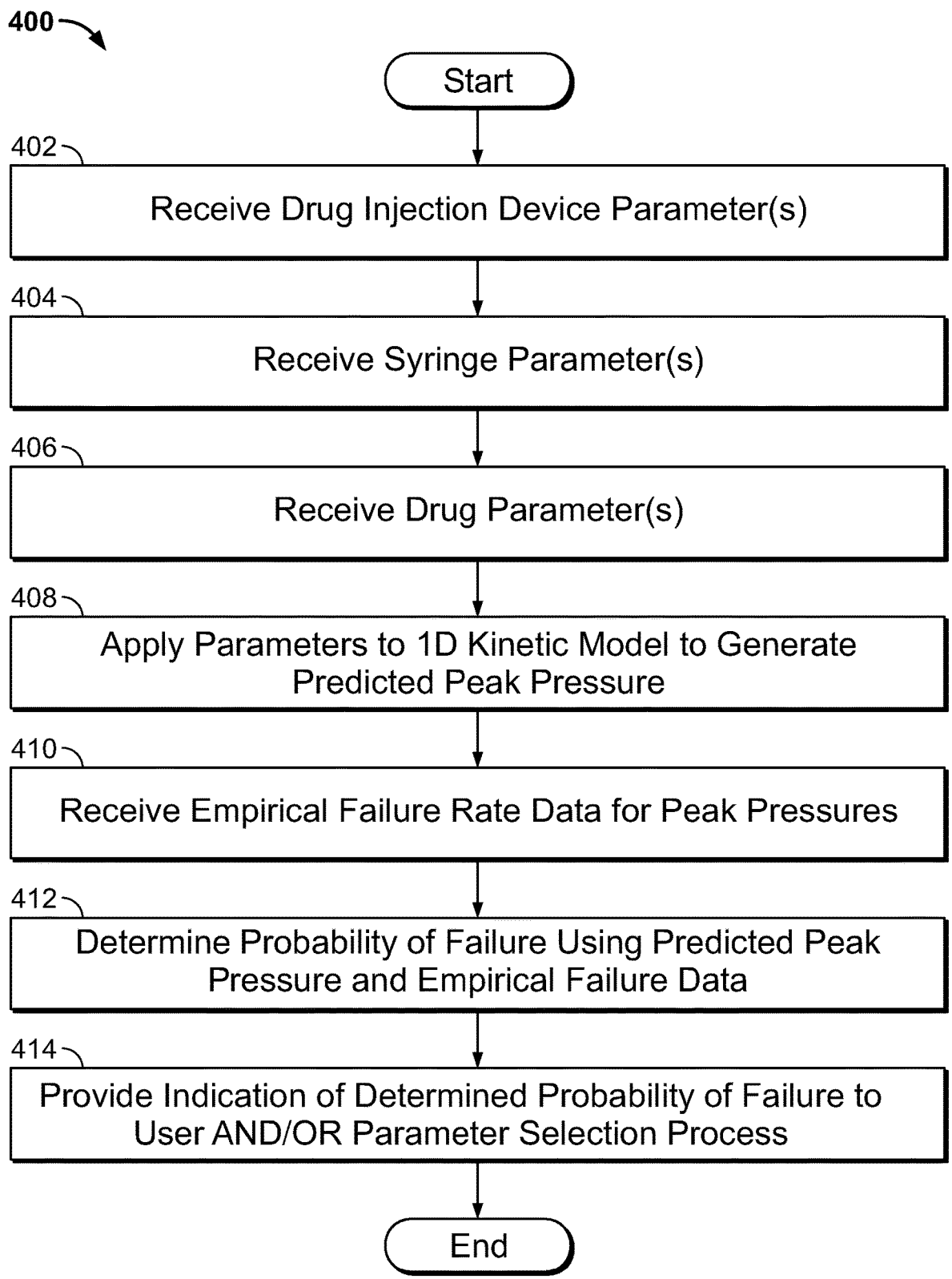
FIG. 12 is a flow diagram of an example method for determining predicted failure rates of drug injection devices, which can be implemented in the system of FIG. 1.

FIG. 12 is a flow diagram of an example method for determining predicted failure rates of drug injection devices. The method can be implemented in the modeling system 30, for example. More generally, the method 400 can be implemented as a set of instructions stored on a non-transitory computer-readable medium and executable on one or more processors.

The method 400 begins at block 402, where parameters for a drug injection device are received. At blocks 404 and 406, parameters for a syringe and a drug, respectively, are received. As discussed above, these parameters can include geometric inputs related to the plunger, plunger depth, the syringe, spring length, etc.; mass parameters related to the syringe, the plunger, the spring, etc.; visco-elastic input parameters; etc.

Some or all of these parameters can be received via the user interface of the parameter selection module 50. Some parameters, such as damping constants, can be derived using experimental data as discussed above. Further, in some scenarios, some of the input parameters are generated automatically in an iterative manner so as to generate and subsequently compare respective outputs. For example, the parameter selection module 50 can iterate through multiple values of the plunger depth in a certain range [$D_1$, $D_2$], with a step S, while keeping the other parameters the same (or adjusted only in view of the change to the plunger depth). The injector modeling module 32 can generate respective predicted peak pressure values for each value of the plunger depth and determine which values produce acceptable results, which values produce optimal results, etc. If desired, the parameter selection module 50 can automatically adjust multiple parameters at the same time when seeking an acceptable set of configuration parameters.

With continued reference to FIG. 12, the received parameters are applied to the model to generate a predicted pressures at block 408. Next, at block 410, experimental (empirical) data for peak pressures are received. Generally speaking, the experimental values can be obtained in any suitable manner, and can vary in quality depending on the number of samples tested, how well the parameters of the tested devices correspond to the input parameters into the model, etc.

The probability of failure is determined at block 412 using predicted peak pressure output by the model and the empirical data received at block 410. To this end, the two-term Weibull distribution, or another suitable statistical technique, can be applied.

Next, at block 414, an indication of the determine probability of failure is provided to a user via a user interface, or the determined probability of failure can be used in an automated process to modify one or several parameters and re-apply the parameters to the model. The latter approach is discussed in more detail below with reference to FIG. 13.

Figure 13:
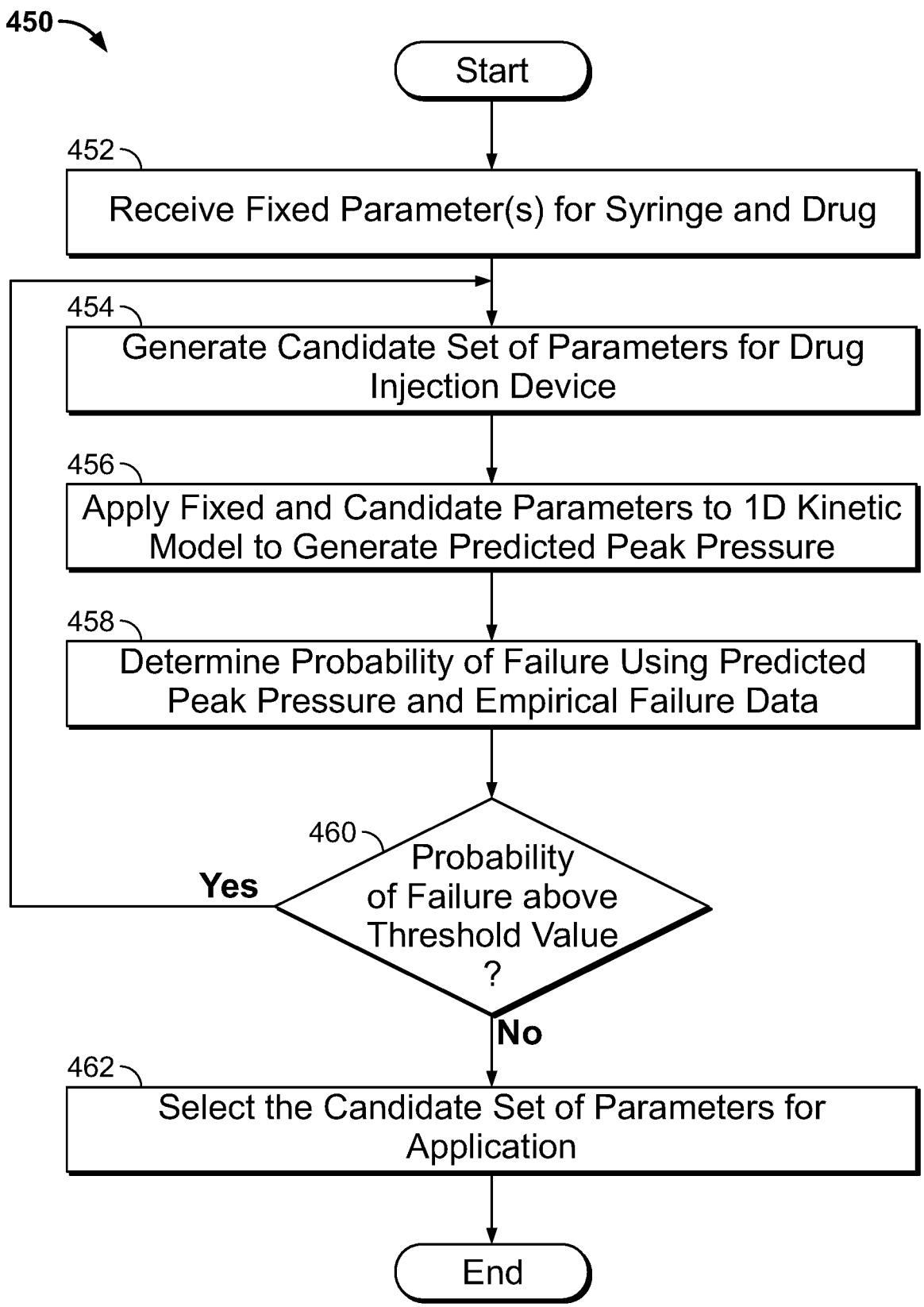
FIG. 13 is a flow diagram of an example method for manufacturing a drug injection device using the system of FIG. 1.

Now referring to FIG. 13, a method 450 also can be implemented in the modeling system 30 as a set of instructions stored on a non-transitory computer-readable medium and executable on one or more processors. The method 450 is applicable to drug injection devices such as the autoinjector 100 discussed above.

The method 450 begins at block 452, where a set of "fixed" parameters are received. For example, an operator using the system 30 can decide to fix the parameters of the syringe and the drug for various business reasons, and decide to vary only the parameters of the drug injection device. Of course, the operator can also fix some of the parameters of the drug injection device (or at least impose certain narrow restrictions on these parameters, such as small ranges of permissible values).

At block 454, a candidate set of parameters for the drug injection device is received. Some of these parameters may be generated automatically. At block 456, the parameters obtained at block 452 and 454 are applied to the 1D kinematic model to generate peak pressure, and probability of failure is determined using the predicted peak pressure and empirical data at block 458 (similar to the method 400 discussed above).

The resulting probability is then compared to a certain threshold value at block 460. If the probability is determined to be acceptable, the flow proceeds to block 462, where the set of parameters applied to the model is selected as an acceptable configuration. Otherwise, if the probability is determined to exceed the threshold and accordingly deemed unacceptable, the flow returns to block 454, where a new set of candidate parameters is generated (or received from an operator, in an alternative scenario).

More particularly, as a result of executing block 462, improvement actions can be initiated. For example, the design of the autoinjector can be modified to reduce pressure within the syringe. According to one example scenario, a different needle can be used to reduce the required extrusion force of the drug, which in turn permits using a lower-force spring. The method completes after executing block 462.

Additional Considerations

It should be understood that the above-described techniques can be used with various devices that deliver, or utilize in operation, high-viscosity liquids. These devices include but are not limited to auto-injectors, and the high-viscosity liquids include but are not limited to drugs. Thus, although The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U. S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP 1Ib/IIa receptor monoclonal antibody); Actemra® (anti-IL6 Receptor mAb); Avastin® (bevacizumab), HuMax-CD4

(zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracia protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the computing system for modeling and parameter selection, drug injection device, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the computing systems, drug delivery devices, systems, methods, and their elements.

What is claimed is:

1. A non-transitory computer-readable medium storing thereon instructions that, when executed on one or more processors, implement a method for determining predicted failure rates of drug injection devices, the method comprising:
receiving a set of parameters that specify physical properties of (i) a syringe, and (ii) a liquid drug, and (iii) a drug injection device configured to deliver the liquid drug to a patient via the syringe, wherein the drug injection device includes a mechanism configured to drive a plunger rod toward a plunger of the syringe encased in a syringe carrier;
receiving failure rate data that specifies a measured rate of failure of the drug injection device in response to various peak pressures within the syringe;
applying the received set of parameters to a one-dimensional (1D) kinematic model of the drug injection device to determine a predicted peak pressure within the syringe, including determining the predicted peak pressure as a function of impact velocity of the liquid drug, and including using the 1D kinematic model to model interactions between at least the mechanism, the plunger rod, the plunger, and the syringe carrier, wherein using the 1D kinematic model includes (A) modeling the mechanism as a linear spring with an equilibrium length, and/or (B) modeling (i) a pre-impact stage at which the plunger rod has not come in contact with the plunger, and (ii) a first impact stage at which the plunger rod comes in contact with the plunger;
determining a probability of failure of the drug injection device using (i) the received failure rate data and (ii) the predicted peak pressure; and
providing an indication of the determined probability of failure to an output device.

2. The computer-readable medium of claim 1, wherein the implemented method further comprises modeling a fluid column in the syringe as an acoustic medium.

3. The computer-readable medium of claim 1, wherein the implemented method further comprises modeling a fluid column in the syringe using a Korteweg equation.

4. The computer-readable medium of claim 1, wherein using the 1D kinematic model includes modeling (i) the pre-impact stage at which the plunger rod has not come in contact with the plunger, (ii) the first impact stage at which the plunger rod comes in contact with the plunger, and (iii) a third impact stage at which the syringe carrier comes in contact with a front shell.

5. The computer-readable medium of claim 1, wherein receiving the set of parameters to the 1D kinematic model includes receiving geometric parameters related to at least one of the syringe or the drug injection device, including at least one of: (i) plunger depth, (ii) plunger rod wall thickness, (iii) plunger rod activation length, (iv) syringe barrel diameter, (v) syringe wall thickness, (vi) fluid volume, (vii) syringe carrier activation length, (viii) plunger rod depth, (ix) length of the guide rod, (x) length of guide rod base, (xi) length of needle insertion, (xii) needle length, (xiii) needle, or (xiv) un-sprung length of spring.

6. The computer-readable medium of claim 1, wherein receiving the set of parameters to the 1D kinematic model includes receiving parameters indicative of masses of components, including at least one of: (i) mass of syringe carrier, (ii) mass of pre-filled syringe with drug, (iii) mass of plunger, (iv) mass of rod, or (iv) mass of spring.

7. The computer-readable medium of claim 1, wherein receiving the set of parameters to the 1D kinematic model includes receiving at least one of the following (a) through (e):
(a) a parameter indicative of plunger elasticity,
(b) a parameter indicative of fluid sound speed,
(c) a parameter indicative of viscosity of the drug,
(d) a spring constant, and/or
(e) experimental data indicative of a plurality of test runs of an actual drug injector device that shares at several physical properties with the drug injection device being modeled, and deriving one or more of (i) syringe driver friction, (ii) internal plunger damping, and (iii) plunger-syringe friction.

8. The computer-readable medium of claim 1, wherein determining the probability of failure of the drug injection device includes applying a two-term Weibull distribution function.

9. A method for manufacturing drug injection devices, the method comprising:
receiving, by one or more processors, a fixed set of parameters that specify physical properties of a syringe and a liquid drug;
determining a set of parameters that specify physical properties of a drug injection device configured to deliver the liquid drug to a patient via the syringe, wherein the drug injection device includes a mechanism configured to drive a plunger rod toward a plunger of the syringe encased in a syringe carrier, wherein determining the set of parameters includes:
(i) generating, by the one or more processors, a candidate set of parameters for the drug injection device,
(ii) applying, by the one or more processors, the fixed set of parameters and the candidate set of parameters to a one-dimensional (1D) kinematic model of the drug injection device to determine a predicted peak pressure within the syringe, including determining the predicted peak pressure as a function of impact velocity of the liquid drug, and including using the 1D kinematic model to model interactions between at least the mechanism, the plunger rod, the plunger, and the syringe carrier, wherein using the 1D kinematic model includes (A) modeling the mechanism as a linear spring with an equilibrium length, and/or (B) modeling (i) a pre-impact stage at which the plunger rod has not come in contact with the plunger, and (ii) a first impact stage at which the plunger rod comes in contact with the plunger,
(iii) determining, by the one or more processors, a probability of failure of the drug injection device using the determined predicted peak pressure,
(iv) if the probability of failure is above a threshold value, repeating the steps (i)-(iii) with a modified candidate set of parameters, and
(v) selecting the candidate set of parameters if the probability of failure is not above the threshold value; and
manufacturing the drug injection device using the determined set of parameters.

10. The method of claim 9, further comprising modeling a fluid column in the syringe as an acoustic media.

11. The method of claim 9, further comprising modeling a fluid column in the syringe using a Korteweg equation.

12. The method of claim 9, wherein using the 1D kinematic model includes modeling (i) the pre-impact stage at which the plunger rod has not come in contact with the plunger, (ii) the first impact stage at which the plunger rod comes in contact with the plunger, and (iii) a third impact stage at which the syringe carrier comes in contact with a front shell.

13. The method of claim 9, wherein receiving the set of parameters that specify the physical properties of the drug injection device includes receiving at least one of the following (a) through (g):
   (a) geometric parameters for one or several components of the drug injection device,
   (b) parameters indicative of masses of components of the drug injection device
   (c) a parameter indicative of plunger elasticity,
   (d) a parameter indicative of fluid sound speed,
   (e) a parameter indicative of viscosity of the drug,
   (f) a spring constant, and/or
   (g) experimental data indicative of a plurality of test runs of an actual drug injector device that shares at several physical properties with the drug injection device being modeled, and deriving one or more of (i) syringe driver friction, (ii) internal plunger damping, and (iii) plunger-syringe friction.

14. A drug injection device configured to deliver a liquid drug to a patient via a syringe, the drug injection device prepared by a process comprising:
   receiving a fixed set of parameters that specify physical properties of a syringe and a liquid drug;
   determining a set of parameters that specify physical properties of a drug injection device configured to deliver the liquid drug to a patient via the syringe, wherein the drug injection device includes a mechanism configured to drive a plunger rod toward a plunger of the syringe encased in a syringe carrier, and wherein determining the set of parameters includes:
   (i) generating a candidate set of parameters for the drug injection device;
   (ii) applying the fixed set of parameters and the candidate set of parameters to a one-dimensional (1D) kinematic model of the drug injection device to determine a predicted peak pressure within the syringe, including determining the predicted peak pressure as a function of impact velocity of the liquid drug, and including using the 1D kinematic model to model interactions between at least the mechanism, the plunger rod, the plunger, and the syringe carrier, wherein using the 1D kinematic model includes (A) modeling the mechanism as a linear spring with an equilibrium length, and/or (B) modeling (i) a pre-impact stage at which the plunger rod has not come in contact with the plunger, and (ii) a first impact stage at which the plunger rod comes in contact with the plunger,
   (iii) determining a probability of failure of the drug injection device using the determined predicted peak pressure,
   (iv) if the probability of failure is above a threshold value, repeating the steps (i)(iii) with a modified candidate set of parameters, and
   (v) selecting the candidate set of parameters if the probability of failure is not above the threshold value; and
   using the determined set of parameters to manufacture the drug injection device.

15. The drug injection device of claim 14, wherein the process further comprises modeling a fluid column in the syringe as an acoustic media.

16. The drug injection device of claim 14, wherein the process further comprises modeling a fluid column in the syringe using a Korteweg equation.

\* \* \* \* \*

UNITED STATES PATENT AND TRADEMARK OFFICE
CERTIFICATE OF CORRECTION

PATENT NO. : 11,200,298 B2
APPLICATION NO. : 16/070224
DATED : December 14, 2021
INVENTOR(S) : Sean Fitzgibbon et al.

It is certified that error appears in the above-identified patent and that said Letters Patent is hereby corrected as shown below:

On the Title Page

At Page 2, item (56), under "OTHER PUBLICATIONS", Line 2, "electricity",Medical" should be -- elasticity, Medical ... --.

In the Specification

At Column 5, Line 66, "needle shield 120," should be -- needle shield 126, --.

At Column 6, Line 8, "is occurs" should be -- occurs --.

At Column 6, Line 9, "plunger rod 100" should be -- plunger rod 110 --.

At Column 6, Line 18, "plunger 120." should be -- plunger 112. --.

At Column 6, Line 19, "plunger 120" should be -- plunger 112 --.

At Column 6, Line 20, "plunger 120" should be -- plunger 112 --.

At Column 6, Line 48, "glass syringe 100," should be -- glass syringe 120, --.

At Column 6, Line 58, "plunger rod 112" should be -- plunger rod 110 --.

At Column 7, Line 10, "form" should be -- from --.

At Column 7, Line 16, "syringe carrier 114" should be -- syringe carrier 122 --.

At Column 15, Line 24, "the this" should be -- this --.

At Column 16, Line 19, "used)," should be -- used); --.

Signed and Sealed this
Twenty-seventh Day of June, 2023

Katherine Kelly Vidal
*Director of the United States Patent and Trademark Office*

CERTIFICATE OF CORRECTION (continued)
U.S. Pat. No. 11,200,298 B2

At Column 16, Line 57, "signal-to-noise (SNR)" should be -- signal-to-noise ratio (SNR) --.

At Column 19, Lines 48-49, "drugs. Thus, although" should be -- drugs. --.

At Column 20, Line 4, "(methyoxy" should be -- (methoxy --.

At Column 21, Line 11, "(denosamab);" should be -- (denosumab); --.

At Column 21, Line 13, "filgastrim," should be -- filgrastim --.

At Column 21, Line 41, "chimaeric" should be -- chimeric --.

At Column 21, Line 42, "chimaeric" should be -- chimeric --.

In the Claims

At Column 29, Line 37, in Claim 1, "data" should be -- data, --.

At Column 30, Line 3, in Claim 6, "(iv)" should be -- (v) --.

At Column 31, Line 16, in Claim 13, "device" should be -- device, --.

At Column 32, Line 4, in Claim 14, "device;" should be -- device, --.

At Column 32, Line 24, in Claim 14, "(i)(iii)"should be -- (i)-(iii) --.